(12) United States Patent
Parker et al.

(10) Patent No.: US 10,444,060 B2
(45) Date of Patent: Oct. 15, 2019

(54) FLUID CONTAINER MEASUREMENT SYSTEM

(71) Applicant: Adaptec Medical Devices LLC, Tucson, AZ (US)

(72) Inventors: Walter Dan Parker, Tucson, AZ (US); Edward James Mueller, San Antonio, TX (US); Keith Hobart Gausmann, Cary, NC (US); Nathan Thomas Luck, Apex, NC (US); Scott Eric Liddle, Raleigh, NC (US)

(73) Assignee: ADAPTEC MEDICAL DEVICES LLC, Tucson, AZ (US)

( * ) Notice: Subject to any disclaimer, the term of this patent is extended or adjusted under 35 U.S.C. 154(b) by 0 days.

(21) Appl. No.: 15/961,376

(22) Filed: Apr. 24, 2018

(65) Prior Publication Data

US 2018/0245967 A1   Aug. 30, 2018

Related U.S. Application Data

(63) Continuation-in-part of application No. 15/489,215, filed on Apr. 17, 2017, now Pat. No. 9,995,619.
(Continued)

(51) Int. Cl.
*G01G 19/00* (2006.01)
*G01G 19/14* (2006.01)
(Continued)

(52) U.S. Cl.
CPC ............. *G01G 19/14* (2013.01); *A61B 5/208* (2013.01); *A61F 5/44* (2013.01); *G01G 17/04* (2013.01);
(Continued)

(58) Field of Classification Search
CPC ........ G01G 19/14; G01G 17/04; G01G 19/18; G01G 21/23; G01G 23/00; G01G 23/18;
(Continued)

(56) References Cited

U.S. PATENT DOCUMENTS 3,147,813 A   9/1964   Rezaeih
3,360,062 A   12/1967   Potter
(Continued)

FOREIGN PATENT DOCUMENTS

CN   203539798 U   4/2014
CN   107106095 A   8/2017
(Continued)

OTHER PUBLICATIONS

Anwar, Haroon, "Urinfo 2000 Precise Urine Meter from Flowsense," medGadget, Oct. 20, 2010, 4 pages.
(Continued)

*Primary Examiner* — Max H Noori
(74) *Attorney, Agent, or Firm* — Withrow & Terranova, PLLC

(57) ABSTRACT

A fluid container measurement system is disclosed. The fluid container measurement system is configured to suspend a load measurement assembly a distance above a support surface. The load measurement assembly houses a load cell and a measurement control circuit. The measurement control circuit is coupled to the load cell and configured to receive electrical signals indicative of a force imposed on the load cell. Electrical signals generated by the load cell indicative of the force exerted on the load cell can be used to measure the fluid container attached to the load cell linkage member.

58 Claims, 29 Drawing Sheets

Related U.S. Application Data

(60) Provisional application No. 62/335,939, filed on May 13, 2016, provisional application No. 62/468,687, filed on Mar. 8, 2017.

(51) Int. Cl.

| | | |
|---|---|---|
| *G01V 8/10* | (2006.01) | |
| *G01G 21/23* | (2006.01) | |
| *G01G 17/04* | (2006.01) | |
| *A61F 5/44* | (2006.01) | |
| *A61B 5/20* | (2006.01) | |
| *G01G 23/18* | (2006.01) | |
| *G01G 19/18* | (2006.01) | |
| *G01G 23/00* | (2006.01) | |
| *A61M 25/00* | (2006.01) | |
| *G08B 21/18* | (2006.01) | |

(52) U.S. Cl.
CPC .............. *G01G 19/18* (2013.01); *G01G 21/23* (2013.01); *G01G 23/00* (2013.01); *G01G 23/18* (2013.01); *G01V 8/10* (2013.01); *A61M 25/0017* (2013.01); *G08B 21/182* (2013.01)

(58) Field of Classification Search
CPC . A61B 5/208; A61F 5/44; G01V 8/10; A61M 25/0017; G08B 21/182
USPC ..................................... 73/862.68; 74/862.68
See application file for complete search history.

(56) References Cited

U.S. PATENT DOCUMENTS

| | | |
|---|---|---|
| 3,783,866 A | 1/1974 | Tirkkonen |
| 3,933,212 A | 1/1976 | Bradley et al. |
| 4,026,151 A | 5/1977 | Fitzgerald |
| 4,198,626 A | 4/1980 | Rauscher |
| 4,457,750 A | 7/1984 | Hill |
| 4,559,821 A | 12/1985 | Engeler et al. |
| 4,606,420 A | 8/1986 | Silver |
| 4,678,049 A | 7/1987 | Gummere et al. |
| 4,712,567 A | 12/1987 | Gille et al. |
| 4,805,460 A | 2/1989 | Betterton et al. |
| 5,003,488 A | 3/1991 | Hardy |
| 5,492,537 A | 2/1996 | Vancaillie |
| 5,522,805 A | 6/1996 | Vancaillie et al. |
| 5,629,498 A | 5/1997 | Pollock et al. |
| 5,709,670 A | 1/1998 | Vancaillie et al. |
| 5,756,940 A | 5/1998 | Van Driel et al. |
| 5,769,087 A | 6/1998 | Westphal et al. |
| 5,850,757 A | 12/1998 | Wierenga |
| 5,921,953 A | 7/1999 | Novak et al. |
| 5,944,668 A | 8/1999 | Vancaillie et al. |
| 5,956,130 A | 9/1999 | Vancaillie et al. |
| 6,044,699 A | 4/2000 | Greenblatt et al. |
| 6,121,555 A | 9/2000 | Nowosielski et al. |
| 6,302,864 B1 | 10/2001 | Nowosielski |
| 6,528,739 B1 | 3/2003 | Nowosielski et al. |
| 6,590,167 B2 | 7/2003 | Clare |
| 6,690,280 B2 | 2/2004 | Citrenbaum et al. |
| 7,207,966 B2 | 4/2007 | Savare et al. |
| 7,591,945 B2 | 9/2009 | Meziere et al. |
| 7,603,894 B2 | 10/2009 | Breed |
| 7,611,496 B2 | 11/2009 | Yamada et al. |
| 7,789,850 B2 | 9/2010 | Roger |
| 7,819,003 B2 | 10/2010 | Breed et al. |
| 7,899,616 B2 | 3/2011 | Breed |
| 8,075,513 B2 | 12/2011 | Rudko et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,731 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,209,195 B2 | 6/2012 | Dicks et al. |
| 8,209,941 B2 | 7/2012 | Osborne et al. |
| 8,214,549 B2 | 7/2012 | Dicks et al. |
| 8,262,602 B2 | 9/2012 | Lee et al. |
| 8,327,890 B2 | 12/2012 | Mackrill et al. |
| 8,331,239 B2 | 12/2012 | Yamada |
| 8,403,875 B2 | 3/2013 | Peters et al. |
| 8,444,623 B2 | 5/2013 | Gelfand et al. |
| 8,579,859 B2 | 11/2013 | Kramer et al. |
| 8,701,229 B2 | 4/2014 | Lemire et al. |
| 8,708,950 B2 | 4/2014 | Scarpaci et al. |
| 8,730,050 B2 | 5/2014 | Bregeon |
| 8,738,322 B1 | 5/2014 | Gioffre, II et al. |
| 8,777,897 B2 | 7/2014 | Butterfield |
| 8,954,719 B2 | 2/2015 | Dicks et al. |
| 8,966,235 B2 | 2/2015 | Dicks et al. |
| 9,050,422 B2 | 6/2015 | Coelho et al. |
| 9,074,920 B2 | 7/2015 | Mendels et al. |
| 9,078,971 B2 | 7/2015 | Scarpaci et al. |
| 9,157,786 B2 | 10/2015 | Fulkerson et al. |
| 9,177,476 B2 | 11/2015 | Breed |
| 9,347,817 B2 | 5/2016 | Pollock et al. |
| 9,995,619 B2 | 6/2018 | Parker et al. |
| 10,010,031 B1 * | 7/2018 | Liu ........................ A01G 25/06 |
| 2004/0260232 A1 | 12/2004 | Cimino |
| 2006/0064053 A1 | 3/2006 | Bollish et al. |
| 2007/0106177 A1 | 5/2007 | Hama |
| 2007/0193379 A1 | 8/2007 | McCluskey |
| 2007/0293827 A1 | 12/2007 | Kim |
| 2008/0073129 A1 | 3/2008 | Heuer |
| 2008/0087475 A1 | 4/2008 | Petrucelli |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0103370 A1 | 5/2008 | Dicks et al. |
| 2008/0103554 A1 | 5/2008 | Dicks et al. |
| 2008/0103555 A1 | 5/2008 | Dicks et al. |
| 2008/0151759 A1 | 6/2008 | Yamada |
| 2008/0172021 A1 | 7/2008 | Dijkman |
| 2008/0183502 A1 | 7/2008 | Dicks et al. |
| 2008/0186205 A1 | 8/2008 | Breed |
| 2008/0215120 A1 | 9/2008 | Dicks et al. |
| 2008/0215202 A1 | 9/2008 | Breed |
| 2008/0215231 A1 | 9/2008 | Breed |
| 2008/0215360 A1 | 9/2008 | Dicks et al. |
| 2008/0216567 A1 | 9/2008 | Breed |
| 2008/0218376 A1 | 9/2008 | Dicks et al. |
| 2008/0224852 A1 | 9/2008 | Dicks et al. |
| 2008/0236275 A1 | 10/2008 | Breed et al. |
| 2009/0115628 A1 | 5/2009 | Dicks et al. |
| 2009/0234672 A1 | 9/2009 | Dicks et al. |
| 2010/0224841 A1 | 9/2010 | Liljedahl |
| 2011/0066555 A1 | 3/2011 | Dicks et al. |
| 2011/0078441 A1 | 3/2011 | Dicks et al. |
| 2011/0090086 A1 | 4/2011 | Dicks et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0158430 A1 | 6/2011 | Dicks et al. |
| 2011/0161111 A1 | 6/2011 | Dicks et al. |
| 2011/0167250 A1 | 7/2011 | Dicks et al. |

(56) References Cited

U.S. PATENT DOCUMENTS

| | | |
|---|---|---|
| 2011/0179405 A1 | 7/2011 | Dicks et al. |
| 2011/0205074 A1 | 8/2011 | Feng et al. |
| 2011/0213621 A1 | 9/2011 | Dicks et al. |
| 2011/0282671 A1 | 11/2011 | Dicks et al. |
| 2011/0319813 A1 | 12/2011 | Kamen et al. |
| 2012/0000713 A1 | 1/2012 | Taboada |
| 2012/0006599 A1 | 1/2012 | Murdter |
| 2012/0118650 A1 | 5/2012 | Gill |
| 2013/0060211 A1 | 3/2013 | Adams, Jr. |
| 2013/0066644 A1 | 3/2013 | Dicks et al. |
| 2013/0150821 A1 | 6/2013 | Bollish et al. |
| 2013/0177455 A1* | 7/2013 | Kamen ............... G06F 19/3418 417/313 |
| 2013/0255282 A1 | 10/2013 | Heston |
| 2014/0051946 A1 | 2/2014 | Arne et al. |
| 2014/0135732 A1 | 5/2014 | Spronken et al. |
| 2014/0174596 A1 | 6/2014 | Lopez et al. |
| 2014/0174835 A1 | 6/2014 | Fulkerson et al. |
| 2014/0243738 A1 | 8/2014 | Kramer et al. |
| 2014/0262918 A1 | 9/2014 | Chu |
| 2014/0311239 A1 | 10/2014 | Marjanovic et al. |
| 2015/0061876 A1 | 3/2015 | Chang |
| 2015/0169314 A1 | 6/2015 | Dicks et al. |
| 2016/0231343 A1 | 8/2016 | Yan et al. |
| 2016/0310045 A1 | 10/2016 | Hoffman et al. |
| 2017/0000946 A1* | 1/2017 | Boyle ................... A61M 5/172 |

FOREIGN PATENT DOCUMENTS

| | | |
|---|---|---|
| DE | 20217847 U1 | 4/2004 |
| EP | 2730215 A1 | 5/2014 |
| WO | 2007148892 A1 | 12/2007 |
| WO | 2009107012 A1 | 9/2009 |
| WO | 2013138537 A9 | 9/2013 |
| WO | 2016103256 A1 | 6/2016 |

OTHER PUBLICATIONS

Author Unknown, "UROS Automated Urine Output and Temperature Monitoring System," Prescriptive Information, bardmedical.com/products/patient-monitoring-systems/uros%E2%84%A2-automated-urine-output-and-temperature-monitoring-system/, accessed Mar. 23, 2017, C.R. Bard, Inc., 6 pages.

Author Unknown, "Bard Uros: Automated Urine Output and Temperature Monitor," Operator's Manual, Model: BK, Oct. 2016, C.R. Bard, Inc., 52 pages.

Invitation to Pay Additional Fees for International Patent Application No. PCT/US2017/027920, dated Jan. 26, 2018, 14 pages.

International Search Report and Written Opinion for PCT/US2017/027920, dated Mar. 26, 2018, 18 pages.

Notice of Allowance for U.S. Appl. No. 15/489,215, dated Jan. 26, 2018, 7 pages.

International Preliminary Report on Patentability for PCT/US2017/027920, dated Nov. 22, 2018, 11 pages.

Extended European Search Report for European Patent Application No. 18208964.9, dated Mar. 27, 2019, 5 pages.

* cited by examiner

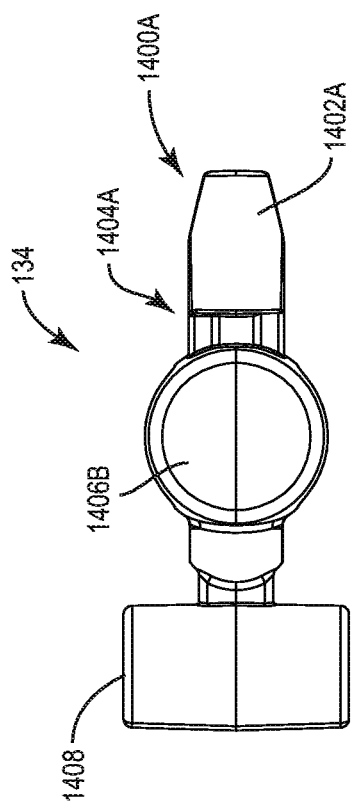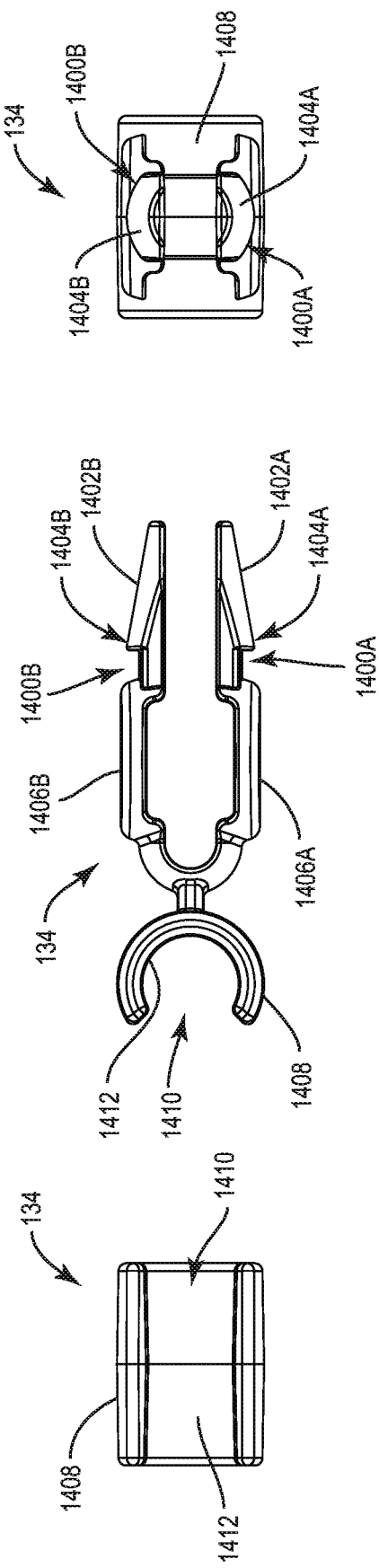
FIG. 15D
FIG. 15B
FIG. 15A
FIG. 15C

FLUID CONTAINER MEASUREMENT SYSTEM

PRIORITY APPLICATIONS

The present application is a continuation-in-part of U.S. Non-provisional patent application Ser. No. 15/489,215 filed on Apr. 17, 2017 entitled "Fluid Container Measurement System Employing Load Cell Linkage Member," issued as U.S. Pat. No. 9,995,619, which claims priority to both U.S. Provisional Patent Application Ser. No. 62/335,939 filed on May 13, 2016 entitled "Fluid Container Measurement System Employing Load Cell Linkage Member," and also U.S. Provisional Patent Application Ser. No. 62/468,687 filed on Mar. 8, 2017 entitled "Fluid Container Measurement System Employing Load Cell Linkage Member," the contents of which are incorporated herein by reference in their entirety.

BACKGROUND

I. Field of the Disclosure

The technology of the disclosure relates to monitoring fluid in a container, and more particularly to monitoring and measurement of a biomedical fluid, such as for example, urine collected in a fluid drainage container or bag from a patient using a urinary (Foley) catheter.

II. Background

In medical care settings such as hospitals and other medical facilities, it is often necessary to dispense fluid to patients. For example, an intravenous (IV) bag may be used to store saline or other fluid that is injected into a patient's veins. It is also common in medical care settings to collect fluids from patients. As an example, a urine bag may be connected to a urinary (Foley) catheter to collect urine output from a patient when the catheter is inserted into the patient's bladder. In a post-surgical setting such as intensive care, urine output of the patient is stored in a plastic bag ("urine bag") and monitored periodically as part of monitoring of the patient's physiological parameters to determine if the parameters are within acceptable values or ranges. Monitoring of urine output is a good indication of the state of a patient's kidneys and overall fluid balance of the patient. Further, other fluid output from the patient may also be collected and monitored in a medical setting to monitor the state of health of the patient.

In the example of monitoring of a patient's urine output, it is common practice for the patient's urine output to be measured every hour. To facilitate this monitoring, the urine bag may have certain visual indicators such as volume lines that can be used to determine if the patient's urine output has increased, and if so, by what volume. The reading of the urine bag must be monitored and recorded. This requires going to the patient's bed, visually observing the urine bag, taking a measurement of urine output based on the visual observation since the last measurement, and writing the measurement of urine output into a log or documentation sheet or manually entering the measurement into an electronic medical record. Further, the urine bag may have to be emptied. This process can take substantial time, and thus, the frequency of measuring urine output may be determined more by convenience of staff schedules rather than strict physiological reasons.

Accordingly, it would be advantageous to provide a way to monitor fluid delivered from or stored in a container or bag, including in a medical setting, in an automated manner to avoid the imprecision of monitoring frequency and accuracy performed by a human being.

SUMMARY OF THE DISCLOSURE

Aspects disclosed in the detailed description include a fluid container measurement system employing a load cell linkage member. In this regard, the fluid container measurement system includes a load measurement assembly configured to be suspended a distance above a support surface. The load measurement assembly houses a load cell and a measurement control circuit. The measurement control circuit is coupled to the load cell and configured to receive electrical signals indicative of a force imposed on the load cell. The load measurement assembly also includes or is configured to receive a load cell linkage member mechanically linked to the load cell. In this manner, a load placed on the load cell linkage member will be exerted on the load cell. Electrical signals generated by the load cell indicative of the force exerted on the load cell can be used to measure the fluid container attached to the load cell linkage member.

In one aspect, the load measurement assembly also includes a load cell interconnect mechanically linked to the load cell, and a measurement electrical interface coupled to the measurement control circuit. The load cell linkage member is provided in the form of a disposable load cell linkage member that includes a support member configured to support a fluid container to be measured, such as a fluid bag, for example. The disposable load cell linkage member is configured to be attached to the load cell interconnect of the load measurement assembly to mechanically link the support member of the load cell linkage member to the load cell for measuring the fluid container supported by the support member. The load cell linkage member also includes a disposable member electrical interface coupled to a disposable member electrical circuit disposed therein. The load cell linkage member and the load measurement assembly are also configured such that their electrical interfaces are electrically coupled to each other when the load cell linkage member is attached to the load cell interconnect, and the support member of the load cell linkage member is positioned within a designed angular range about a principal load axis of the load cell. In this manner, a load placed on the support member will be known to exert a force within a known angle tolerance range about the principal load axis of the load cell for a more accurate weight or volume measurement. The measurement control circuit can be configured to not measure the fluid container attached to the support member of the load cell linkage member until the measurement control circuit can confirm coupling of the electrical interfaces via communication with the disposable member electrical circuit. Thus, the force exerted by the fluid container on the load cell can be more accurately translated into an actual estimated weight or volume of the fluid container, as opposed to using differential measurements, for example.

Providing the disposable member electrical circuit and disposable member electrical interface in a load cell linkage member can also advantageously allow for other non-limiting features. For example, the measurement control circuit may be configured to perform a calibration of the load cell linkage member in response to the detection of the coupling of the electrical interfaces between the load measurement assembly and the load cell linkage member. Because the load cell linkage member can be detached from the load measurement assembly, and because the measurement control circuit can be configured to detect when the load cell linkage member is secured to the load cell interconnect, the measurement control circuit can be configured to measure the weight on the load cell before and after the load cell linkage member is secured to the load cell interconnect for calibration purposes.

As another example, the disposable member electrical circuit in the load cell linkage member could include a memory that is configured to store an identification indicia. An identification indicia may be pre-stored in the memory of the load cell linkage member. The measurement control circuit in the load measurement assembly may be configured to verify the identification indicia to determine that an authorized load cell linkage member has been attached to the load cell interconnect. The measurement control circuit may be configured to determine if an attached load cell linkage member is authorized before measuring any load placed on the support member of the load cell linkage member.

As another example, the identification indicia stored in the memory of the disposable member electrical circuit in the load cell linkage member could uniquely identify a patient such that a load cell linkage member could be associated with a specific patient. The measurement control circuit could be configured to store fluid measurements in the memory of the load cell linkage member so that there is a built-in log of fluid measurements in the load cell linkage member associated with a particular patient. Because the load cell linkage member is in this example is removable from the load measurement assembly, the load cell linkage member can "follow" the patient. For example, if the patient were moved to another room or area with a different load measurement assembly, and the load cell linkage member specific to the patient were attached to the different load measurement assembly, the measurement control circuit in the load measurement assembly could establish the identification of the patient and the fluid measurements previously taken with respect to the patient by communication with the electrical circuit of the load cell linkage member through the coupled interfaces.

Further, in certain aspects disclosed herein, the load measurement assembly may include a wired and/or wireless interface such that the measurement control circuit can be configured to communicate the fluid measurements stored in the load cell linkage member and/or associated with a particular patient through the wired or wireless interface.

Further, in certain aspects disclosed herein, the load measurement assembly may include a tether support member interface configured to receive a tether support member. The tether support member is configured to support a tube from a fluid container so the tube is not strained to unduly impose a force placed on an installed load cell linkage member and thus the load cell. The load cell linkage member may be permanently installed on the load measurement assembly or provided as a load cell linkage member configured to be interconnected with a load cell interconnect of the load cell measurement assembly, including for example as described above. The tether support member is configured to support a predefined length of the tube with the load measurement assembly as part of the weight of the fluid container. The predefined length of the supported portion of the tube can be selected to provide slack in the supported portion of the tube when supported by the tether support member, so that a strain is avoided in the supported portion of the tube. Thus, a force from the load measurement assembly is not imparted on the fluid container from strain. Further, the tether support member may be designed such that a supported portion of the tube will be angled upward so that any fluid contained in the tube is not pooled inside the tube and will be more easily drained to the fluid container.

The tether support member also assists in maintaining the tube at a desired angular orientation to the fluid container such that fluid in the tube is more readily drained to the fluid container through gravity. The tether support member is configured to be secured to the tether support member interface. The tether support member may include an optional electrical interface that is configured to be electrically coupled to the measurement control circuit when the tether support member is installed in the tether support member interface. Thus, the measurement control circuit may be configured to detect when the tether support member is inserted in the tether support member interface. The measurement control circuit may be configured to not measure the force on the load cell if the tether support member is not detected as being inserted in the tether support member interface. The measurement control circuit may also be further configured to detect sudden changes in force on the load cell as an indication that a tube may have been removed from a tether support member when a tether support member was previously detected. In response, the measurement control circuit can be configured to re-calibrate when a tube is reattached to the tether support member.

In another aspect, the measurement control circuit is configured to mitigate any dynamic force transmitted by the tube to the load cell. To do so, in one example, the measurement control circuit is configured to maintain a baseline load measurement of the force on the load cell. Preliminarily, when the measurement control circuit obtains a load measurement from the load cell, the measurement control circuit uses the previous load measurement to determine whether there has been a sudden increase in weight and/or whether there has been a sudden decrease in weight, such as whether a user has removed the bag. If so, the measurement control circuit is configured to generate an alert, including an alert that can be perceived by a user. Otherwise, the measurement control circuit determines whether the load measurement is less than a difference between a previous baseline load measurement and a baseline reset threshold load measurement. If so, then the measurement control circuit is configured to set a new baseline load measurement equal to the load measurement from the load cell, thereby assuming that the measured decrease in load measurement is the result of the dynamic force transmitted from the fluid tube to the load cell. Then, if the load measurement is greater than the previous baseline load measurement plus a noise floor threshold load measurement, the measurement control circuit adds a difference between the load measurement and the previous baseline load measurement to a running total, and sets a new baseline load measurement equal to the load measurement. Accordingly, the measurement control circuit is able to keep a running total measurement while incorporating any dynamic force transmitted from the tube to the load cell. Accounting for this dynamic force prevents the dynamic force of the tube from affecting weight measurement accuracy of the fluid container measurement system, thereby increasing the accuracy of the system. For example, if this dynamic force was ignored or unaccounted for, then real volume increases within the bag may be completely or partially masked by dynamic forces exerted by the tube.

In this regard, in one exemplary aspect, a fluid container measurement system is provided. The fluid container measurement system comprises a load measurement assembly configured to be suspended a distance above a support surface. The load measurement assembly comprises a load cell having a principal load axis substantially orthogonal to the ground. The load measurement assembly also comprises a measurement control circuit electrically coupled to the load cell. The measurement control circuit is configured to receive electrical signals from the load cell indicative of force imposed on the load cell. The load measurement assembly also comprises a measurement electrical interface electrically coupled to the measurement control circuit. The load measurement assembly also comprises a load cell interconnect mechanically linked to the load cell. The fluid container measurement system also comprises a load cell linkage member. The load cell linkage member comprises a disposable member interconnect complementary to the load cell interconnect. The load cell linkage member also comprises a support member configured to support a fluid container. The load cell linkage member also comprises a disposable member electrical circuit, and a disposable member electrical interface electrically coupled to the disposable member electrical circuit. The load cell interconnect is configured to receive the disposable member interconnect to attach the load cell linkage member to the load cell interconnect to provide a mechanical linkage between the support member of the load cell linkage member and the load cell, and dispose the support member of the load cell linkage member within a defined angular range about the principal load axis of the load cell when the disposable member electrical interface is electrically coupled to the measurement electrical interface.

In another exemplary aspect, a method of measuring a fluid container is provided. The method comprises attaching a disposable member interconnect of a load cell linkage member comprising a support member, to a complementary load cell interconnect of a load measurement assembly in an initial position, to mechanically link the load cell linkage member to the load cell interconnect mechanically linked to a load cell having a principal load axis substantially orthogonal to the ground. The method also comprises manipulating the load cell linkage member to place the disposable member interconnect into a measurement position about the load cell interconnect such that a disposable member electrical interface electrically coupled to a disposable member electrical circuit in the load cell linkage member is electrically coupled to a measurement electrical interface electrically coupled to a measurement control circuit in the load measurement assembly wherein the support member is located within a defined angular range about the principal load axis of the load cell. The method also comprises attaching a fluid container to be measured to the support member of the load cell linkage member in the measurement position such that a load of the fluid container applies a force to the load cell through mechanical linkage within the defined angular range about the principal load axis of the load cell when the disposable member electrical interface is electrically coupled to the measurement electrical interface. The method also comprises detecting if the disposable member electrical interface in the load cell linkage member is electrically coupled to the measurement electrical interface in the load measurement assembly. In response to detecting that the disposable member electrical interface is electrically coupled to the measurement electrical interface, the method also comprises the measurement control circuit measuring the fluid container based on an electrical signal received from the load cell indicative of force of the fluid container imposed on the load cell.

In another exemplary aspect, a fluid container measurement system is provided. The fluid container measurement system comprises a load measurement assembly configured to be suspended a distance above a support surface. The load measurement assembly comprises a load cell having a principal load axis substantially orthogonal to the ground. The load measurement assembly also comprises a load cell linkage member mechanically linked to the load cell. The load cell linkage member is configured to support a fluid container such that the force of the fluid container on the load cell linkage member is translated to the load cell. The load measurement assembly also comprises a tether support member interface disposed in a plane above the load cell with respect to the ground. The tether support member interface is configured to provide a tether support member configured to receive a portion of a tube such that a lower portion of the tube of a defined length is disposed above and between the tether support member interface and the fluid container.

In another exemplary aspect, a fluid container measurement system is provided. The fluid container measurement system comprises a load measurement assembly configured to be suspended a distance above a support surface. The load measurement assembly comprises a load cell, a measurement control circuit, a measurement electrical interface, and a load cell interconnect. The load cell has a principal load axis substantially orthogonal to the ground. The measurement control circuit is electrically coupled to the load cell. The measurement control circuit is configured to receive electrical signals from the load cell indicative of force imposed on the load cell. The measurement electrical interface is electrically coupled to the measurement control circuit. The load cell interconnect is mechanically linked to the load cell. The measurement control circuit is configured to obtain a load measurement from the load cell. The measurement control circuit is also configured to, if the load measurement is less than a difference between a previous baseline load measurement and a baseline reset threshold load measurement, set a new baseline load measurement equal to the load measurement. The measurement control circuit is also configured to, if the load measurement is greater than the previous baseline load measurement plus a noise floor threshold, add a difference between the load measurement and the previous baseline load measurement to a running total, and set a new baseline load measurement equal to the load measurement.

In another exemplary aspect, a method of measuring a fluid container is provided. The method comprises attaching a fluid container to be measured to a support member of a load cell linkage member of a load measurement assembly. The load cell linkage member is in a measurement position such that a load of the fluid container applies a force to a load cell through mechanical linkage within a defined angular range about a principal load axis of the load cell. The method further comprises obtaining a load measurement, by a measurement control circuit in the load measurement assembly, by measuring the fluid container based on an electrical signal received from the load cell indicative of force of the fluid container imposed on the load cell. The method further comprises setting, by the measurement control circuit, a new baseline load measurement equal to the load measurement if the load measurement is less than a difference between a previous baseline load measurement and a baseline reset threshold load measurement. The method further comprises adding, by the measurement control circuit, a difference between the load measurement and the previous baseline load measurement to a running total if the load measurement is greater than the previous baseline load measurement plus a noise floor threshold load measurement. The method further comprises setting, by the measurement control circuit, a new baseline load measurement equal to the load measurement if the load measurement is greater than the previous baseline load measurement plus a noise floor threshold load measurement.

BRIEF DESCRIPTION OF THE FIGURES

FIGS. 15A-15D are front, top and bottom, right side, and left side views, respectively, of the tether support member in FIG. 14;

DETAILED DESCRIPTION

Figure 1A:
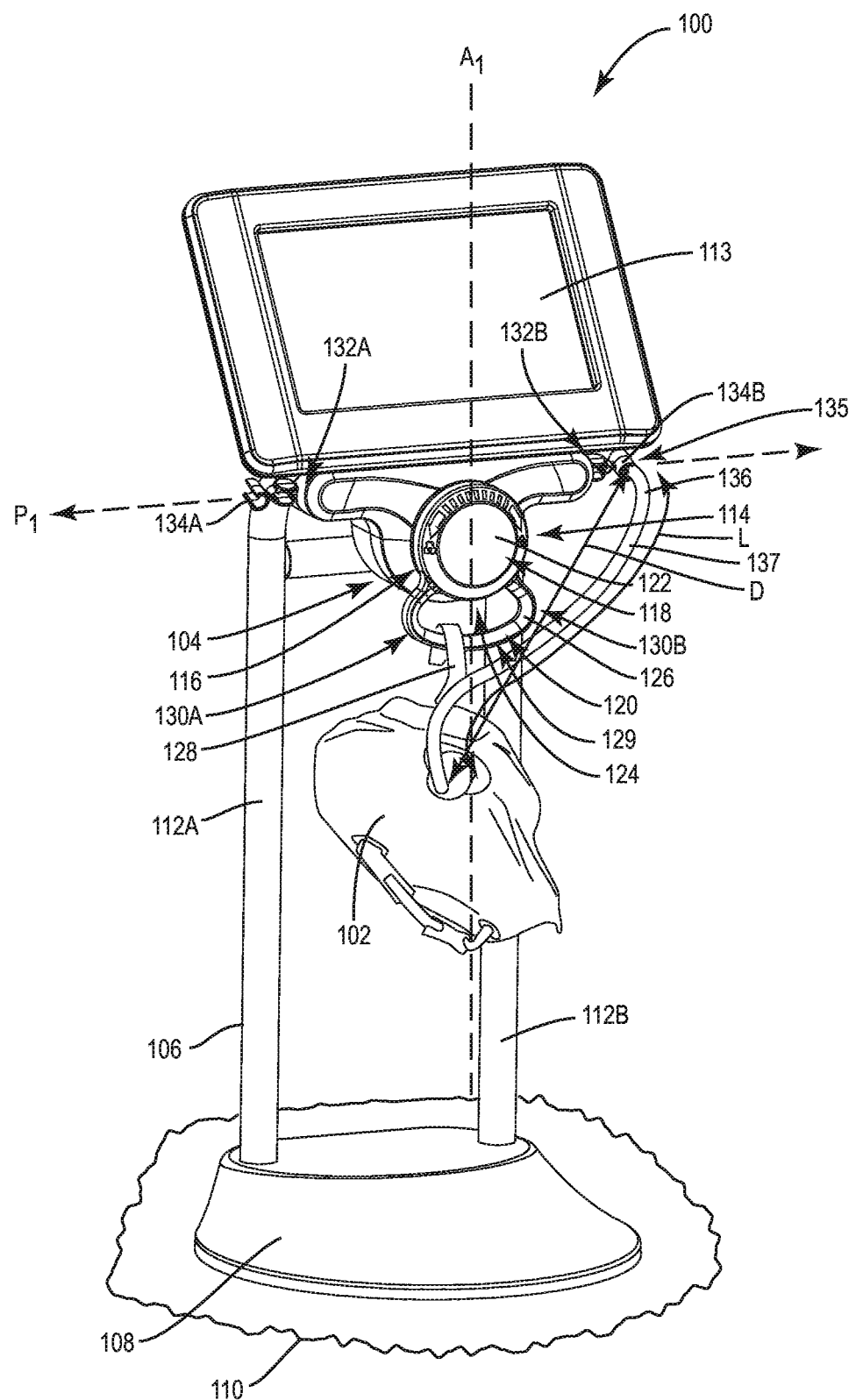
FIG. 1A is an exemplary fluid container measurement system including a load measurement assembly with an installed load cell linkage member having a support member with a fluid container attached thereto, wherein the fluid container measurement system is configured to measure the weight or volume of the fluid container supported by the support member.

With reference now to the drawing figures, several exemplary aspects of the present disclosure are described. The word "exemplary" is used herein to mean "serving as an example, instance, or illustration." Any aspect described herein as "exemplary" is not necessarily to be construed as preferred or advantageous over other aspects.

Figure 1B:
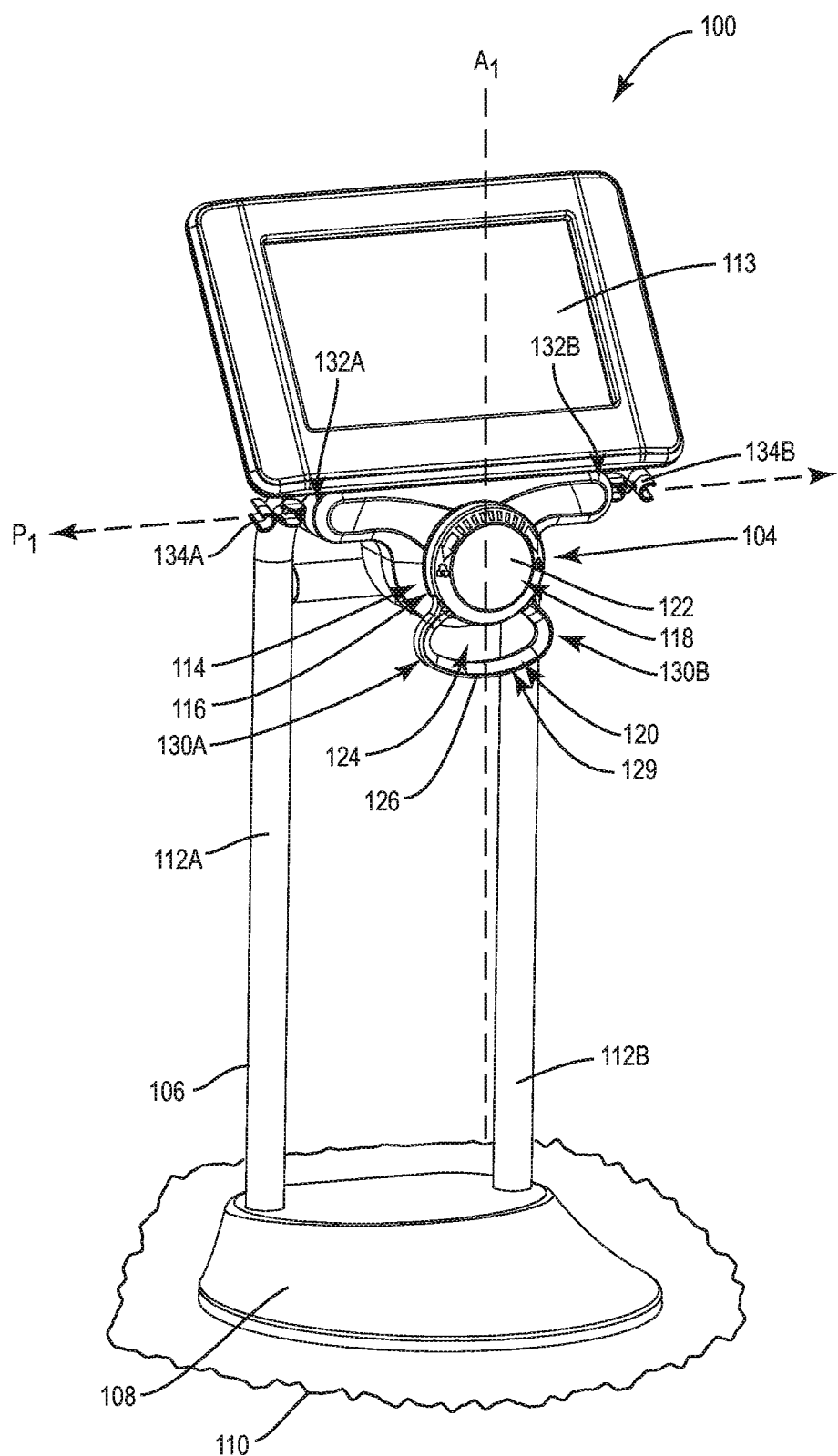
FIG. 1B illustrates the fluid container measurement system in FIG. 1A without the fluid container attached to the load cell linkage member.

FIGS. 1A and 1B illustrate an exemplary fluid container measurement system 100 with a fluid container 102 installed thereon to be measured, and without a fluid container installed to be measured, respectively. As one example, the fluid container 102 may be a urine bag that is fluidly connected to a patient through a Foley catheter. The fluid container measurement system 100 includes a load measurement assembly 104 that is attached to a base assembly 106. The base assembly 106 includes a base 108 that is configured to rest on a support surface 110, such as a table or the floor. For example, it may be desired to place the base 108 on a table beside a medical patient's bed in close proximity to a patient to support the fluid container 102 of a previously catheterized patient or a patient that has been given an intravenous (IV) needle, as examples. Two rails 112A, 112B are inserted into and extend upward in the base 108 away from the support surface 110. The load measurement assembly 104 is attached to the two rails 112A, 112B such that the load measurement assembly 104 is suspended in air a distance above the base 108. In this manner, as shown in FIG. 1A, the fluid container 102 attached to the load measurement assembly 104 is suspended in air above the base 108 so that the force (i.e., weight) of the fluid container 102 is disposed on the load measurement assembly 104. For example, a Foley fluid container may weigh 100 grams when empty and up to 2000 grams when full. The base 108 may also include a counter weight to assist in preventing the fluid container measurement system 100 from tipping over. The base 108 may also allow for the convenient packaging and/or storage of other items for the fluid container measurement system 100, such as circuit boards, cable output and inputs, and a power supply as examples.

As will be discussed in more detail below, the load measurement assembly 104 includes a load cell 114 to measure the fluid container 102, including measuring the weight of the fluid container 102. The load cell 114 is disposed internally in the load measurement assembly 104 in this example and such that the load cell 114 has a principal load axis $A_1$ substantially orthogonal to the ground which is the support surface 110 in this example. Because the base 108 is supported on the support surface 110 in this example, the principal load axis $A_1$ of the load cell 114 is substantially orthogonal to the base 108. In this manner, the fluid container 102 attached to the load measurement assembly 104 exerts a force on the load cell 114 substantially in the principal load axis $A_1$ of the load cell 114 for a more accurate weight measurement. As will be discussed in more detail below, the load measurement assembly 104 also includes a measurement control circuit (not shown) that is electrically coupled to the load cell 114 to receive electrical signals from the load cell 114 indicative of the force applied to the load cell 114. As shown in FIG. 1A, this force includes the weight of the fluid container 102. In this manner, the measurement control circuit can determine the weight of the fluid container 102 in an automated manner without reliance on visual inspection of the fluid container 102. An input device is provided in the form of a display 113 (e.g., a touch screen display) provided in the fluid container measurement system 100 in this example. The measurement control circuit may be configured to support a graphical user interface (GUI) and receive user input (e.g., through a touch screen) through the display 113 to control the operation of the fluid container measurement system 100 and to display information about the measured fluid container 102 attached thereto.

With continuing reference to FIGS. 1A and 1B, as will be discussed in more detail below, the load measurement assembly 104 of the fluid container measurement system 100 includes a load cell interconnect 116 that is mechanically linked to the load cell 114. To provide a linkage member to support the fluid container 102 and also provide a linkage between the weight of the fluid container 102 and the load cell 114 in the load measurement assembly 104, a load cell linkage member 118 is also provided as part of the fluid container measurement system 100. In this example, the load cell linkage member 118 is a disposable load cell linkage member. The load cell linkage member 118 is configured to be removably attached to a complementary the load cell interconnect 116. The load cell linkage member 118 includes a support member 120 that is configured to support the fluid container 102, as is shown in FIG. 1A. Thus, because the load cell linkage member 118 is attached to the load cell interconnect 116, which has a mechanical linkage to the load cell 114, the support member 120 is mechanically linked to the load cell 114. Thus, the force applied by the weight of the fluid container 102 on the support member 120 is applied to the load cell 114, which can be used to determine the weight of the fluid container 102.

In this example, the load cell linkage member 118 has a disc-shaped body 122. The support member 120 is attached or integrally formed with the disc-shaped body 122. The support member 120 has an opening 124 formed by a concave-shaped member 126. Thus, the fluid container 102 can be attached with a hook 128 or other means to the concave-shaped member 126 through the opening 124 to support the weight of the fluid container 102, and impact the weight of the fluid container 102 onto the load cell 114 in the load measurement assembly 104. Further, the opening 124 defines the range of possible angular positions that the fluid container 102 can be disposed relative to the principal load axis $A_1$ of the load cell 114. This may provide for a more accurate and repeatable measurement of the fluid container 102 by limiting the maximum angle and distance that the fluid container 102 can be positioned relative to the principal load axis $A_1$ of the load cell 114. Further, in this example, the concave-shaped member 126 has a center portion 129 closer in distance to the base 108 than end portions 130A, 130B. This may assist in the hook 128, and thus the fluid container 102, being biased towards the principal load axis $A_1$ of the load cell 114, to assist in automatically positioning the fluid container 102 closer to the principal load axis $A_1$ of the load cell 114. Positioning the fluid container 102 closer to the principal load axis $A_1$ f the load cell 114 more accurately disposes the force of the fluid container 102 on the load cell 114 allowing for a more accurate measurement of the fluid container 102.

As will also be discussed in more detail below, the load measurement assembly 104 of the fluid container measurement system 100 in FIGS. 1A and 1B also includes tether support member interfaces 132A, 132B configured to receive and support tether support members 134A, 134B. As shown in FIG. 1A, the tether support members 134A, 134B are configured to support a tube 136 of the fluid container 102 in a support area 135 of the tube 136 with the load measurement assembly 104. This allows a predefined length L of the tube 136 to be supported as a supported portion 137 of the tube 136 by the support member 120 as part of the weight of the fluid container 102. The weight of the supported portion 137 of the tube 136 and the fluid container 102 can also be calibrated during a calibration procedure, as will be discussed in more detail below, so that the weight of the fluid container 102 and the supported portion 137 of the tube 136 is not part of the fluid measurement. Further, the predefined length L of the supported portion 137 of the tube 136 can be selected to provide slack in the supported portion 137 of the tube 136 when supported by the tether support member 134, so that a strain is avoided in the supported portion 137 of the tube 136. Thus, a force from the load measurement assembly 104 is not imparted on the fluid container 102 from strain. Further, in this example, the tether support member 134B supports the tube 136 connected to the fluid container 102 such that the tube 136 is supported in the support area 135 and does not slide or rotate relative to the tether support member 134B.

The tube 136 may have a marking to indicate the position of the support area 135 in which the tube 136 is to be inserted into the tether support member 134B to control the predefined length L of the supported portion 137 of the tube 136 located between the tether support member 134B and the hook 128. The predefined length L of the supported portion of the tube 136 is based on the distance between the tether support member 134A, 134B and the support member 120. If this length L of the supported portion 137 of the tube 136 is too short, a strain force will be imposed on the supported portion 137 of the tube 136. This will cause a force from the load measurement assembly 104 to be imposed on the support portion 137 of the tube 136 and thus also the fluid container 102, which will unduly influence the force on the support member 120 and thus the load cell 114. Further, the tether support members 134A, 134B are designed such that the supported portion 137 of the tube 136 will be angled upward so that any fluid contained in the tube 136 is not pooled inside the tube 136 and will be more easily drained to the fluid container 102 by the fluid container 102 being located a distance D below a plane $P_1$ of the tether support member interfaces 132A, 132B.

Thus, the fluid container measurement system 100 in FIGS. 1A and 1B is a system that is configured to measure the fluid container 102 without the requirement of a person to manually visually observe the fluid level in the fluid container 102. For example, the fluid container measurement system 100 may be used to measure biomedical fluid delivered to or drained from a patient. It is common practice in this example for the patient's urine output to be measured every hour. To facilitate this monitoring, the urine bag must be monitored and recorded. The fluid container measurement system 100 is configured to monitor and measure the fluid container 102 without requiring visual inspection of the fluid container 102 to estimate or guess the weight or volume.

Figure 2A:
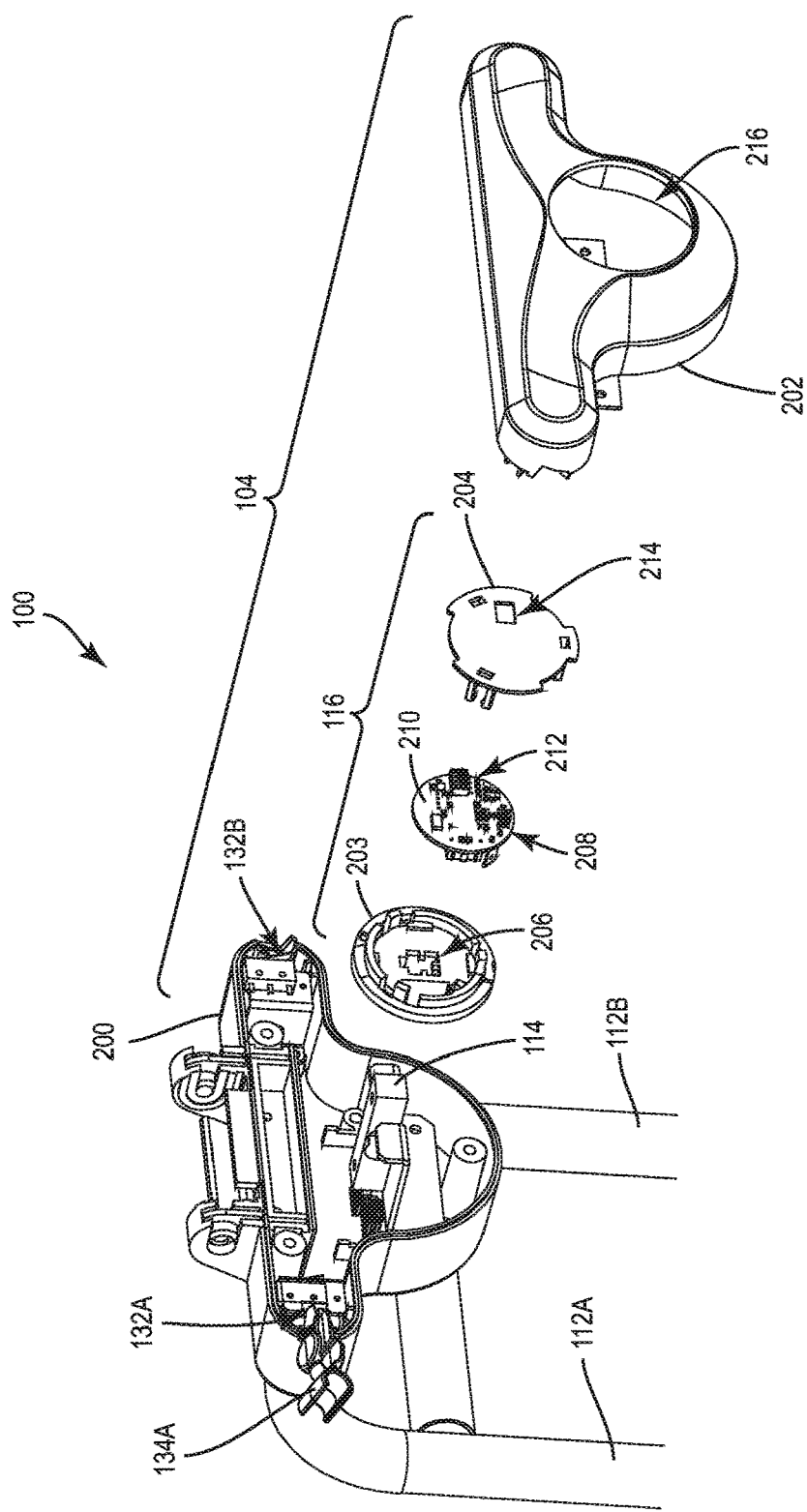
FIG. 2A is an exploded, side perspective view of the load measurement assembly of the fluid container measurement system in FIGS. 1A and 1B.
Figure 2B:
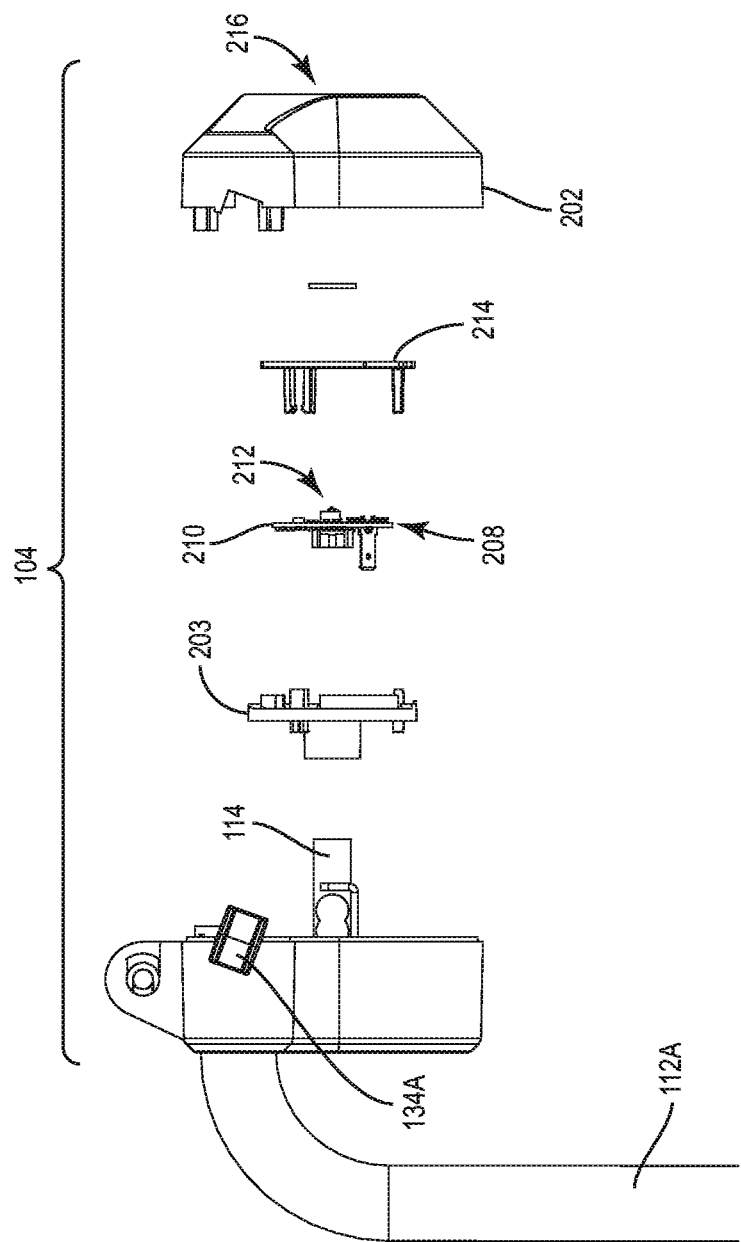
FIG. 2B is an exploded, side view of the load measurement assembly of the fluid container measurement system in FIGS. 1A and 1B.
Figure 3:
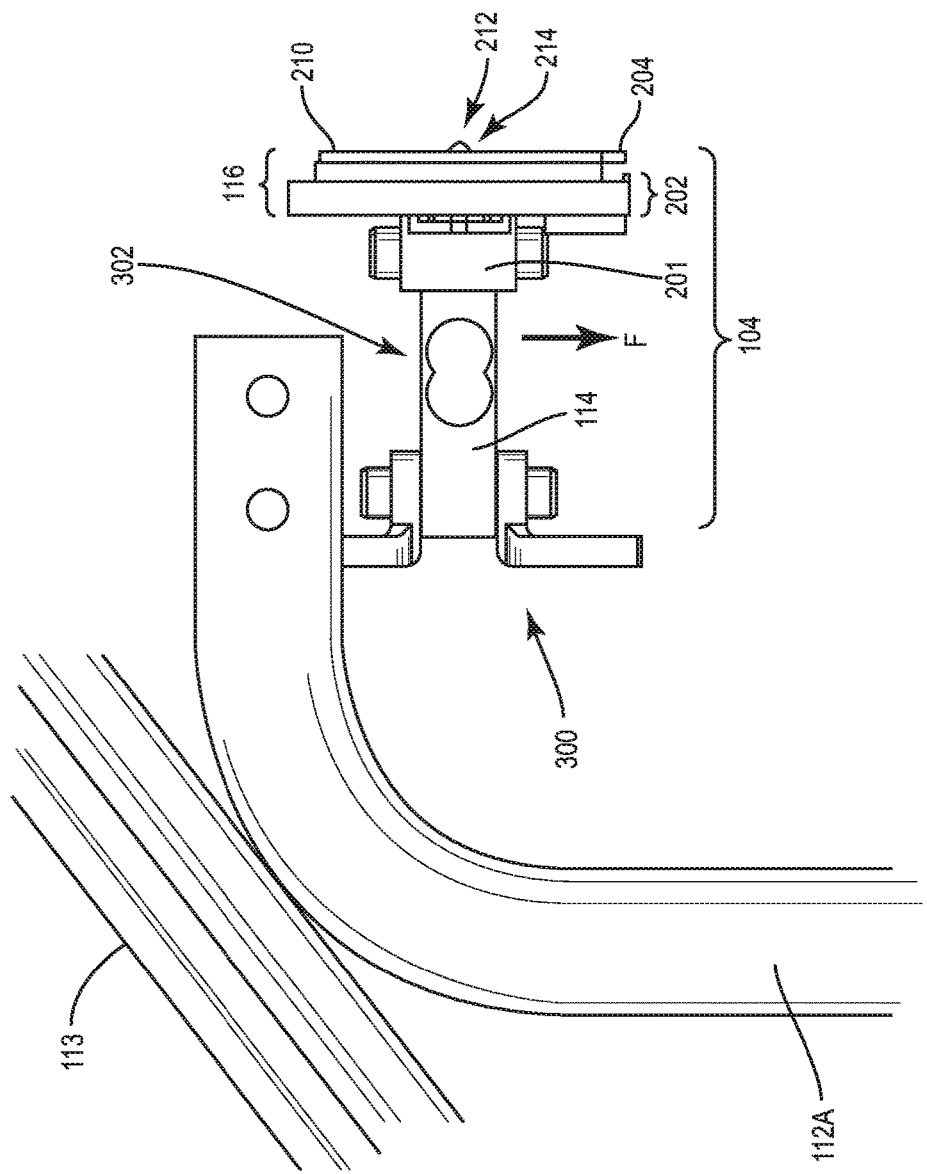
FIG. 3 is a close-up, side internal view of the load measurement assembly of the fluid container measurement system in FIGS. 1A and 1B illustrating a load cell coupled to a load cell interconnect.

To provide more exemplary discussion of the load measurement assembly 104 of the fluid container measurement system 100 in FIGS. 1A and 1B, FIGS. 2A-3 are provided. FIG. 2A is an exploded, side perspective view of the load measurement assembly 104 of the fluid container measurement system 100 in FIGS. 1A and 1B. FIG. 2B is an exploded, side view of the load measurement assembly 104 of the fluid container measurement system in FIGS. 1A and 1B. FIG. 3 is a close-up, side internal view of the load measurement assembly 104 of the fluid container measurement system 100 in FIGS. 1A and 1B illustrating the load cell 114.

As shown in FIGS. 2A and 2B, the load measurement assembly 104 includes a housing 200. The housing contains the load cell 114 and other components, and provides a support mechanism to support the load measurement assembly 104 on the rails 112A, 112B. A cover 202 is also provided that is configured to mate with the housing 200 to secure the load cell 114 and other components inside the load measurement assembly 104. As shown in FIG. 3, the load measurement assembly 104 includes the load cell interconnect 116 that is mechanically linked via linkage 201 to the load cell 114. The load cell 114 is secured to the rails 112A, 112B by an attachment member 300 such that a force F is imparted on a bent section 302 of the load cell 114. The load cell 114 is configured to provide electrical signals to the measurement control circuit 208 (FIGS. 2A and 2B) that can then be used to determine the force applied to the load cell 114 and thus the weight of the fluid container 102 attached to the load cell linkage member 118, as shown in FIG. 1A.

With reference back to FIGS. 2A and 2B, the load cell interconnect 116 is provided by a load cell interconnect shell 203 and a load cell interconnect interface 204 forming a interconnect cavity 206 therein. The load measurement assembly 104 also includes a measurement control circuit 208 as part of the load cell interconnect 116. The measurement control circuit 208 is electrically coupled to the load cell 114 and is configured to receive electrical signals from the load cell 114 indicative of the force imposed on the load cell interconnect 116. The measurement control circuit 208 is disposed on a circuit board 210 (e.g., a printed circuit board (PCB)) secured inside the interconnect cavity 206 of the load cell interconnect 116 in this example. The circuit board 210 also includes a measurement electrical interface 212 that is electrically coupled to the measurement control circuit 208 on the circuit board 210. The load cell interconnect interface 204 includes an opening 214 such that the measurement electrical interface 212 is aligned with the opening 214 and exposed therethrough when the load cell interconnect 116 is fully assembled. As will be discussed in more detail below, the exposed measurement electrical interface 212 is configured to be electrically coupled to a member electrical interface in the load cell linkage member 118 when the load cell linkage member 118 is secured to the load cell interconnect 116 in a measurement position.

Figure 4A:
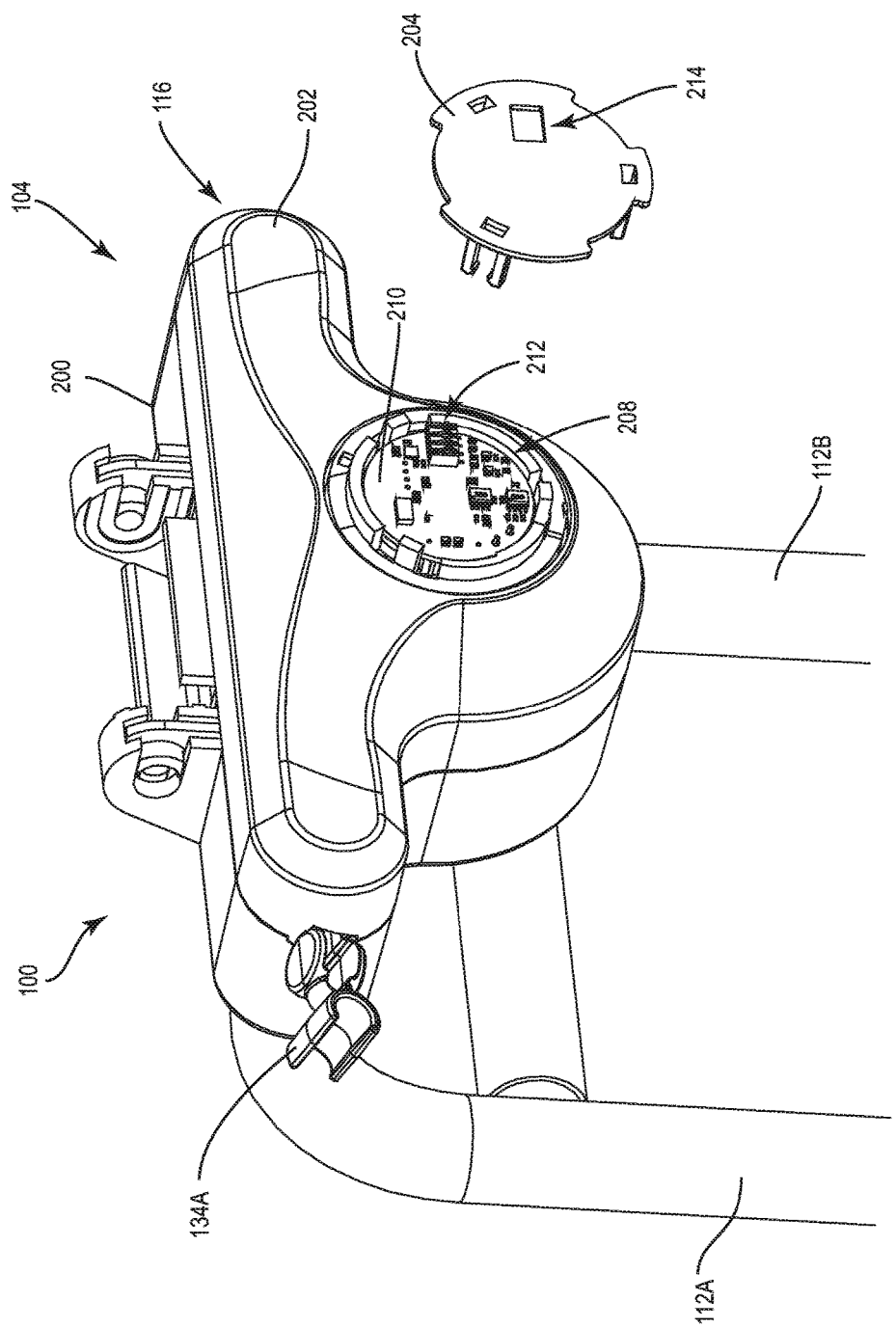
FIG. 4A is a close-up, side perspective view of the load measurement assembly of the fluid container measurement system in FIGS. 1A and 1B illustrating a twist-lock interconnect detached from the load measurement assembly.
Figure 4B:
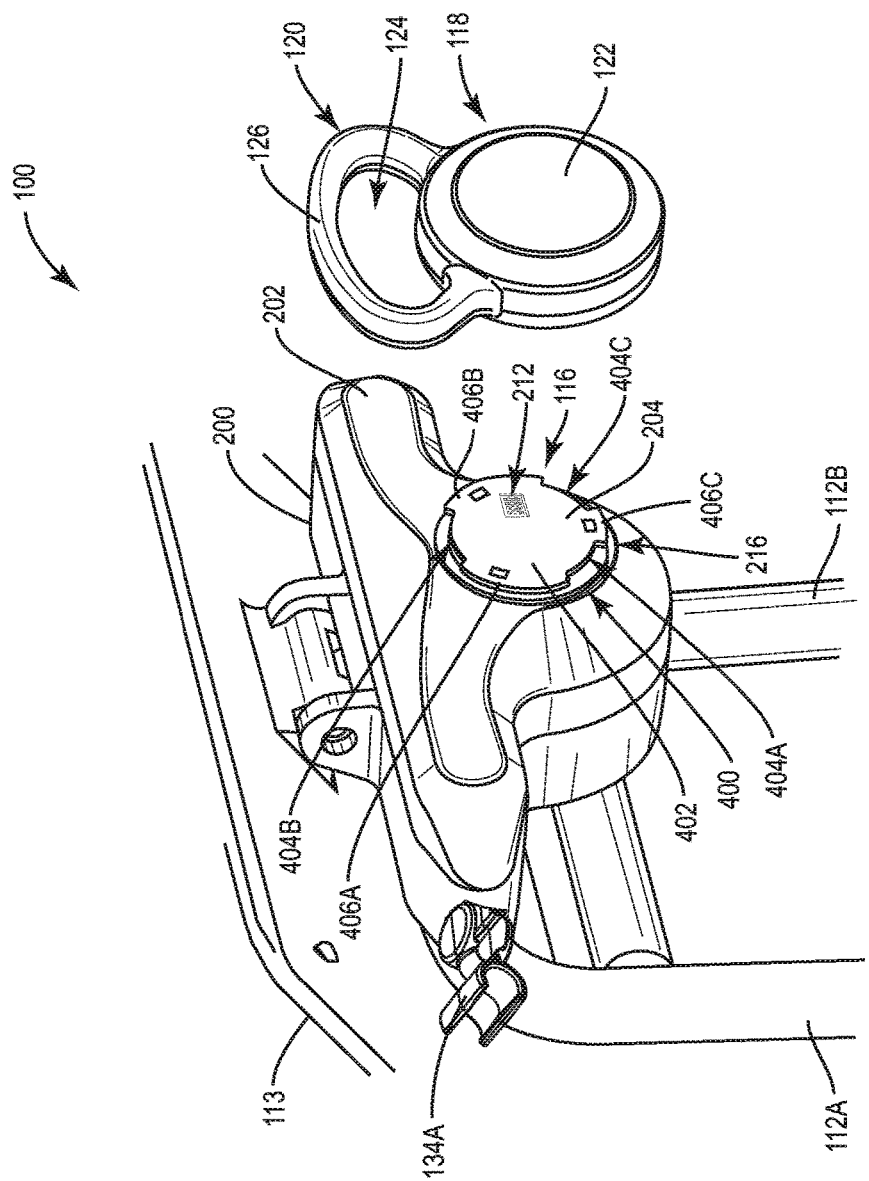
FIG. 4B is a close-up, side perspective view of the load measurement assembly of the fluid container measurement system in FIGS. 1A and 1B illustrating a twist-lock interconnect as part of the load cell interconnect provided in the load measurement assembly to prepare for the load cell linkage member to be installed to the load measurement assembly.

As shown in FIG. 2A, the load cell interconnect 116 is configured to be disposed through an opening 216 in the cover 202 such that the load cell interconnect interface 204 and the measurement electrical interface 212 are exposed through the opening 216, as shown in FIG. 4A. The load cell interconnect interface 204 is exposed through the opening 216 to be configured to attachably receive the load cell linkage member 118 that includes the support member 120, as shown in FIG. 4B. The load cell interconnect 116 is assembled such that the load cell interconnect interface 204 is exposed in the opening 216 as shown in FIG. 4B prepares the load cell interconnect 116 to receive the load cell linkage member 118. When the load cell linkage member 118 is attached to the load cell interconnect 116 as shown in FIGS. 1A and 1B, the load cell linkage member 118 is mechanically linked to the load cell 114 such that the fluid container 102 attached to the support member 120 of the load cell linkage member 118 imposes a force on the load cell 114 that can be analyzed to measure the fluid container 102.

Figure 5A:
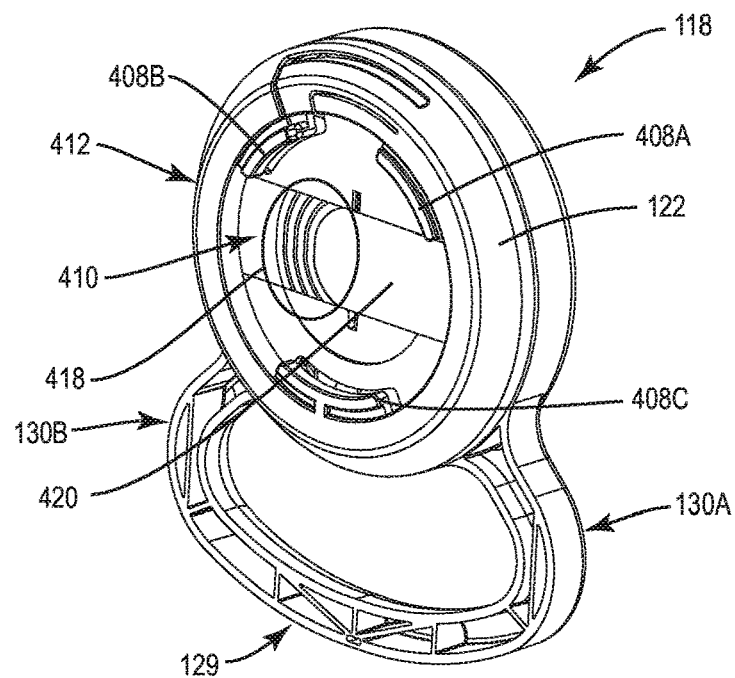
FIGS. 5A and 5B are front and rear perspective views, respectively, of the load cell linkage member.
Figure 5B:
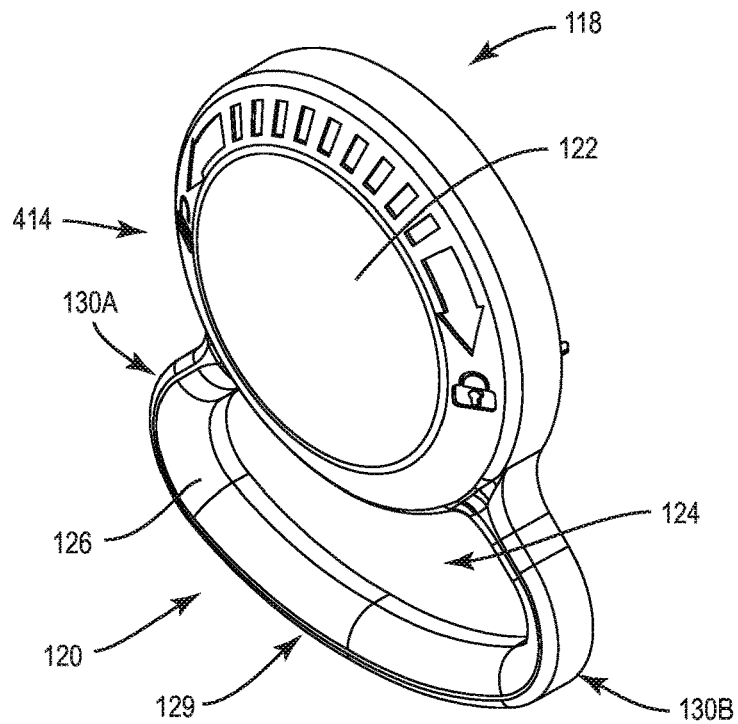
Figure 6:
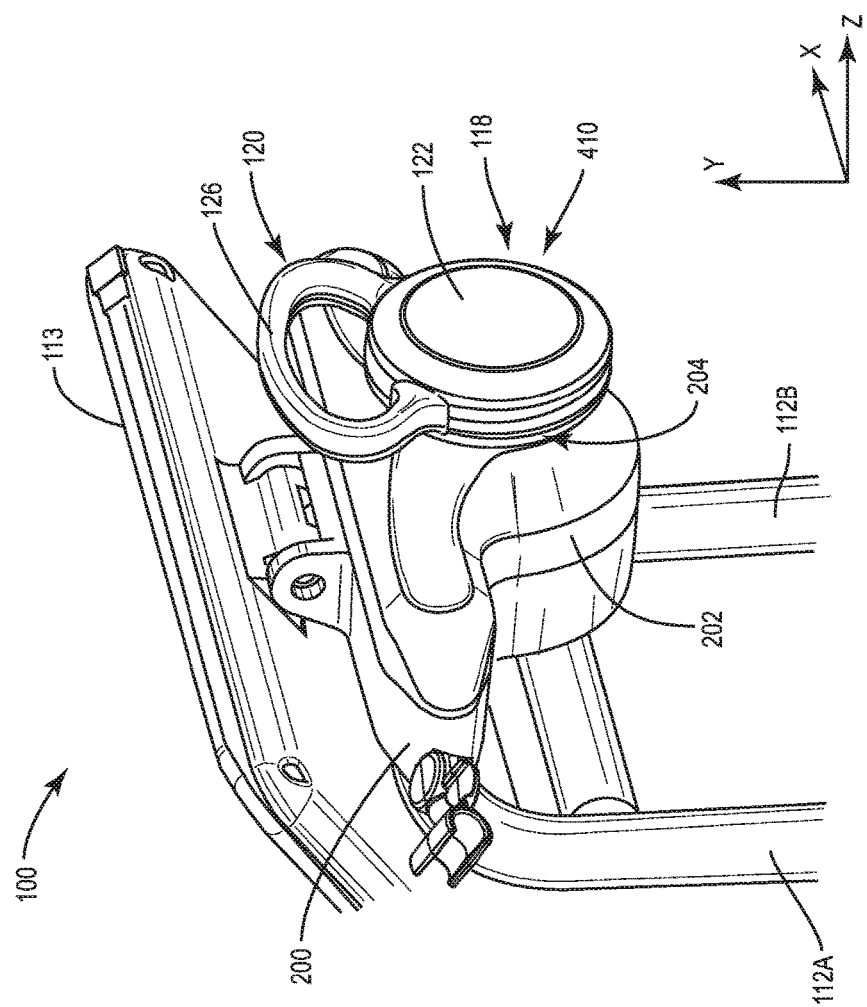
FIG. 6 is a side perspective view of the load cell linkage member in FIGS. 5A and 5B attached in an initial position on the load cell interconnect, wherein electrical interfaces between the load measurement assembly and the load cell linkage member are not electrically coupled to each other.

As shown in FIG. 4B, the load cell interconnect interface 204 of the load cell interconnect 116 includes a locking mechanism 400 which includes a twist-lock interconnect 402 to secure the load cell linkage member 118 to the load cell interconnect 116. The twist-lock interconnect 402 includes a plurality of recesses 404A, 404B, 404C. Tabs 406A, 406B, 406C are formed adjacent to the recesses 404A, 404B, 404C as a result of the recesses 404A, 404B, 404C disposed in the twist-lock interconnect 402. The twist-lock interconnect 402 is configured to receive complementary tabs 408A, 408B, 408C disposed in a disposable member interconnect 410 in a back side 412 of the load cell linkage member 118, as shown in FIG. 5A. The disposable member interconnect 410 is also a complementary twist-lock interconnect to the twist-lock interconnect 402 in this example. A front side 414 of the load cell linkage member 118 is shown in FIG. 5B. The disposable member interconnect 410 in the back side 412 of the load cell linkage member 118 is complementary to the twist-lock interconnect 402 in the load cell interconnect interface 204 in the load cell interconnect 116 of the load measurement assembly 104. To attach the load cell linkage member 118 to the load cell interconnect 116, the back side 412 of the load cell linkage member 118 is positioned with the concave-shaped member 126 disposed concave-downward in an initial position such that the tabs 408A, 408B, 408C of the disposable member interconnect 410 are aligned with the recesses 404A, 404B, 404C of the twist-lock interconnect 402, as shown in FIG. 6. In the initial position, the support member 120 is disposed upward in the Y-direction.

Figure 7:
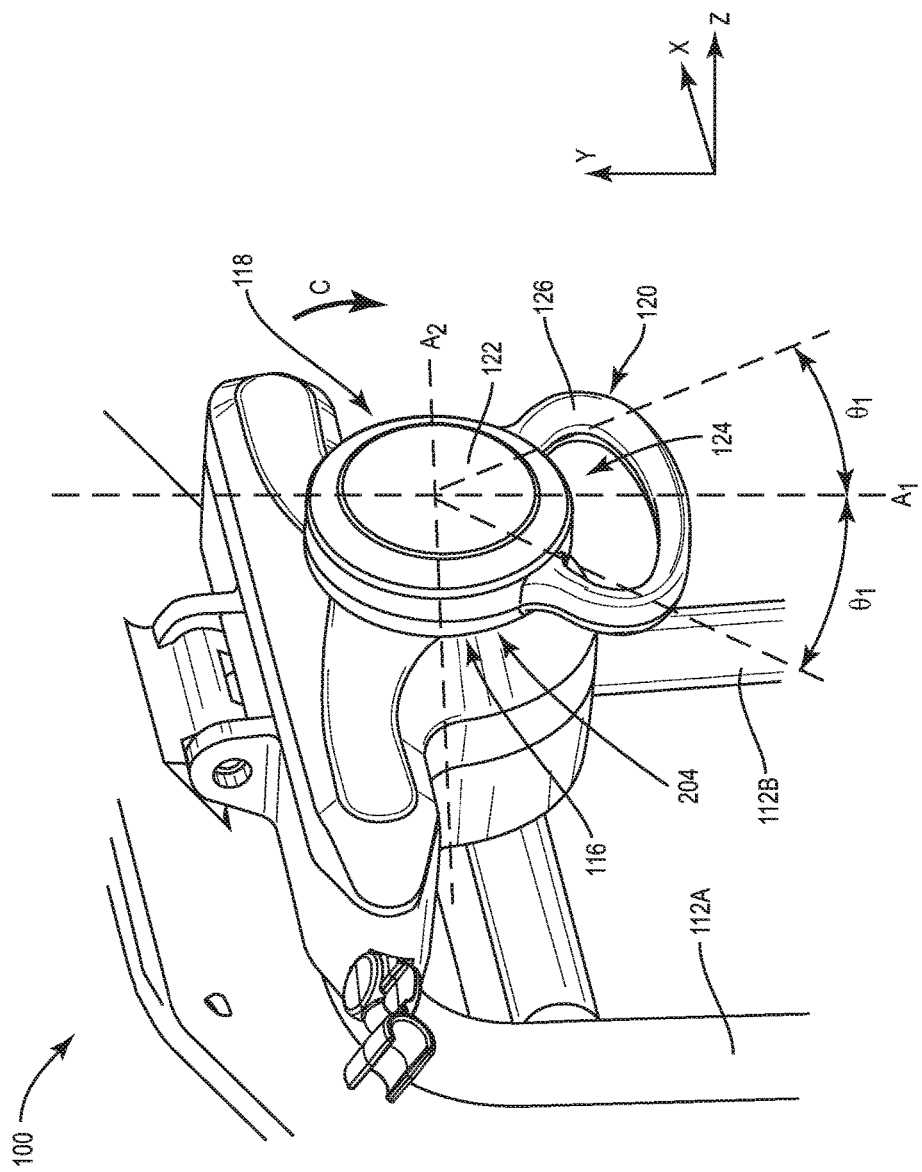
FIG. 7 is a side perspective view of the load cell linkage member in FIGS. 5A and 5B rotated about the load cell interconnect into a measurement position such that electrical interfaces between the load measurement assembly and the load cell linkage member are electrically coupled to each other.
Figure 8:
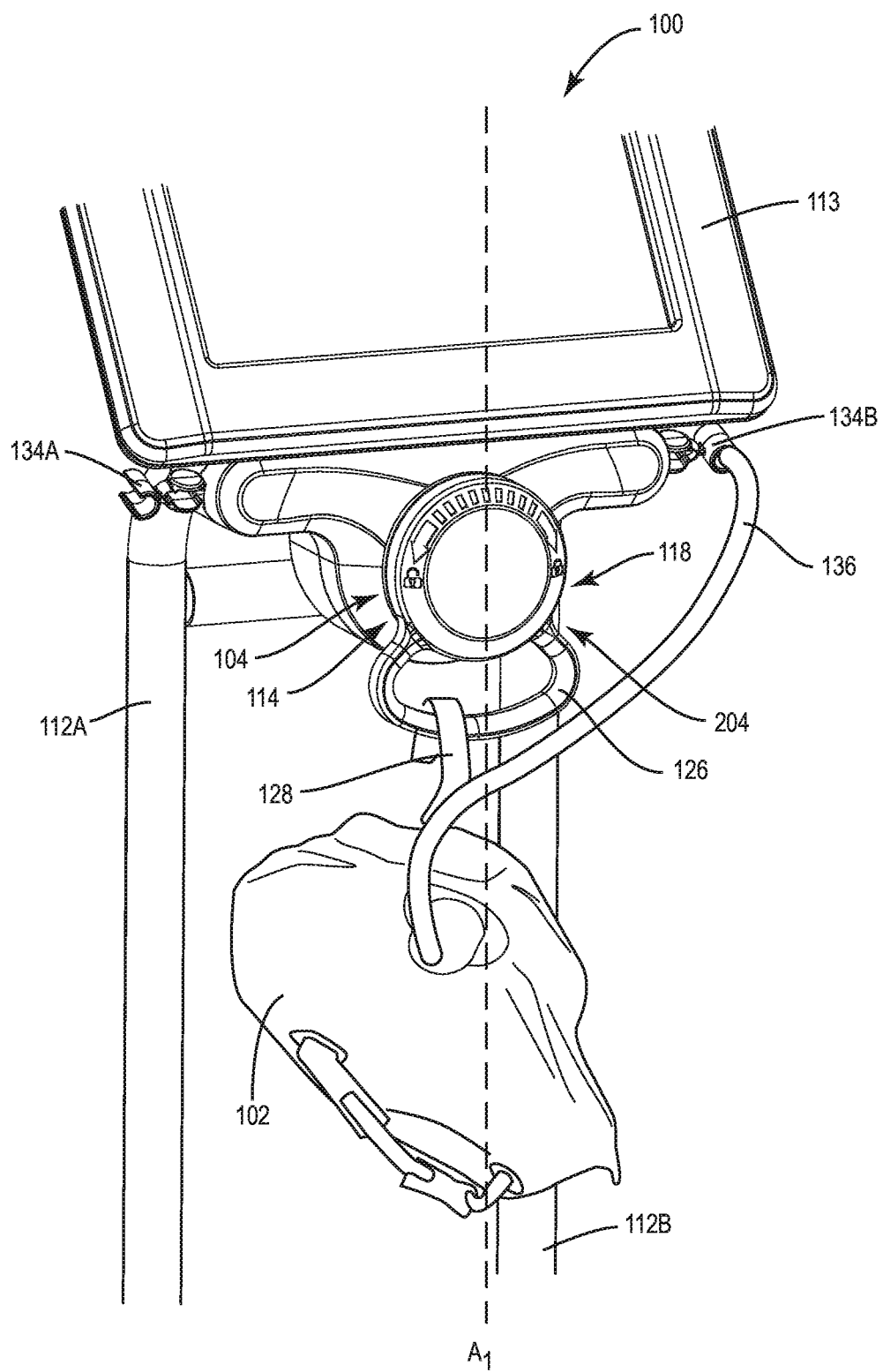
FIG. 8 is a side perspective view of the fluid container measurement system in FIGS. 1A and 1B with an exemplary fluid container attached to a support member of a load cell linkage member installed in a measurement position on a load cell interconnect of a load measurement assembly to prepare for measurement of the fluid container.

As shown in FIG. 7, to secure the load cell linkage member 118 to the load cell interconnect 116 to create a mechanical linkage between the load cell linkage member 118 and the load cell 114, the load cell linkage member 118 is rotated in a clockwise direction C from the initial position in FIG. 6 about the load cell interconnect interface 204 in rotational axis $A_2$. This causes the tabs 408A, 408B, 408C of the disposable member interconnect 410 to be disposed behind the tabs 406A, 406B, 406C of the twist-lock interconnect 402, as shown in FIG. 4B, to form an interference between the tabs 408A, 408B, 408C of the disposable member interconnect 410 and the tabs 406A, 406B, 406C of the twist-lock interconnect 402. In this example, the load cell linkage member 118 is rotated in the clockwise direction C about the load cell interconnect interface 204 approximately 180 degrees from the initial position in FIG. 6, such that the concave-shaped member 126 is disposed concave upward to the ground in a measurement position as shown in FIG. 7. As previously discussed above, the concave-shaped member 126 being disposed downward in the Y direction may assist in the hook 128, and thus the fluid container 102, being biased towards the principal load axis $A_1$ of the load cell 114, to assist in automatically positioning the fluid container 102 closer to the principal load axis $A_1$ of the load cell 114, as shown in FIG. 8. Note that the twist-lock interconnect 402 and disposable member interconnect 410 could be designed such that twisting in an angle different than 180 degrees (e.g., 90 degrees, 45 degrees, etc.) is used to secure the load cell linkage member 118 to the load cell interconnect 116. An alternative connection means to a twist-lock, such as a drop-in connection, may also be employed.

In this example of the fluid container measurement system 100, it is desired to have a method of determining when the load cell linkage member 118 is in the measurement position as shown in FIG. 7. In this regard, as shown back in FIG. 5A, the back side 412 of the load cell linkage member 118 includes a circuit board 416 that includes a disposable member electrical interface 418. The disposable member electrical interface 418 is electrically coupled to a disposable member electrical circuit 420 disposed in the disc-shaped body 122 of the load cell linkage member 118, as shown in FIG. 5A. The disposable member electrical interface 418 is biased to one side of the back side 412 of the disposable member electrical interface 418 such that when the disposable member electrical interface 418 is attached to the load cell interconnect interface 204 in the initial position, the measurement electrical interface 212 disposed therein as shown in FIG. 4A is not electrically coupled to the disposable member electrical interface 418 of the load cell linkage member 118. However, when the load cell linkage member 118 is rotated as discussed above and shown in FIG. 7 into the measurement position, the disposable member electrical interface 418 of the load cell linkage member 118 is electrically coupled to the measurement electrical interface 212 of the load cell interconnect interface 204 of the load cell interconnect 116. The measurement control circuit 208 can communicate over the measurement electrical interface 212, which is coupled to the disposable member electrical interface 418, to the disposable member electrical circuit 420 to detect this connectivity when the load cell linkage member 118 is in the measurement position. This means that the support member 120 of the load cell linkage member 118 is known by the measurement control circuit 208 in the load cell interconnect 116 to be positioned in the downward position, with the support member 120 being able to support the fluid container 102 in a defined angular range +/− $\Theta_1$ about the principal load axis $A_1$ of the load cell 114, as shown in FIG. 7. For example, angle $\Theta_1$ may between approximately one (1) and twenty (20) degrees.

The measurement control circuit 208 in the load cell interconnect 116 may be configured to measure a load disposed on the load cell 114 when the disposable member electrical interface 418 of the load cell linkage member 118 is electrically coupled to the measurement electrical interface 212 of the load cell interconnect interface 204 of the load cell interconnect 116. The measurement control circuit 208 in the load cell interconnect 116 may be configured to not measure the load disposed on the load cell 114 unless the disposable member electrical interface 418 of the load cell linkage member 118 is detected by the measurement control circuit 208 to be electrically coupled to the measurement electrical interface 212 of the load cell interconnect interface 204 of the load cell interconnect 116. Other functionalities can be provided by providing the ability of the measurement control circuit 208 in the load cell interconnect 116 to be able to interface and communicate with the disposable member electrical circuit 420 disposed in the load cell linkage member 118. In this regard, FIG. 9 is a block diagram of an exemplary electronic architecture 900 of the fluid container measurement system 100 in FIGS. 1A and 1B, which shows exemplary detail of the measurement control circuit 208 and the electrical interfaces 212, 418 in the measurement control circuit 208 and the disposable member electrical circuit 420, respectively.

Figure 9:
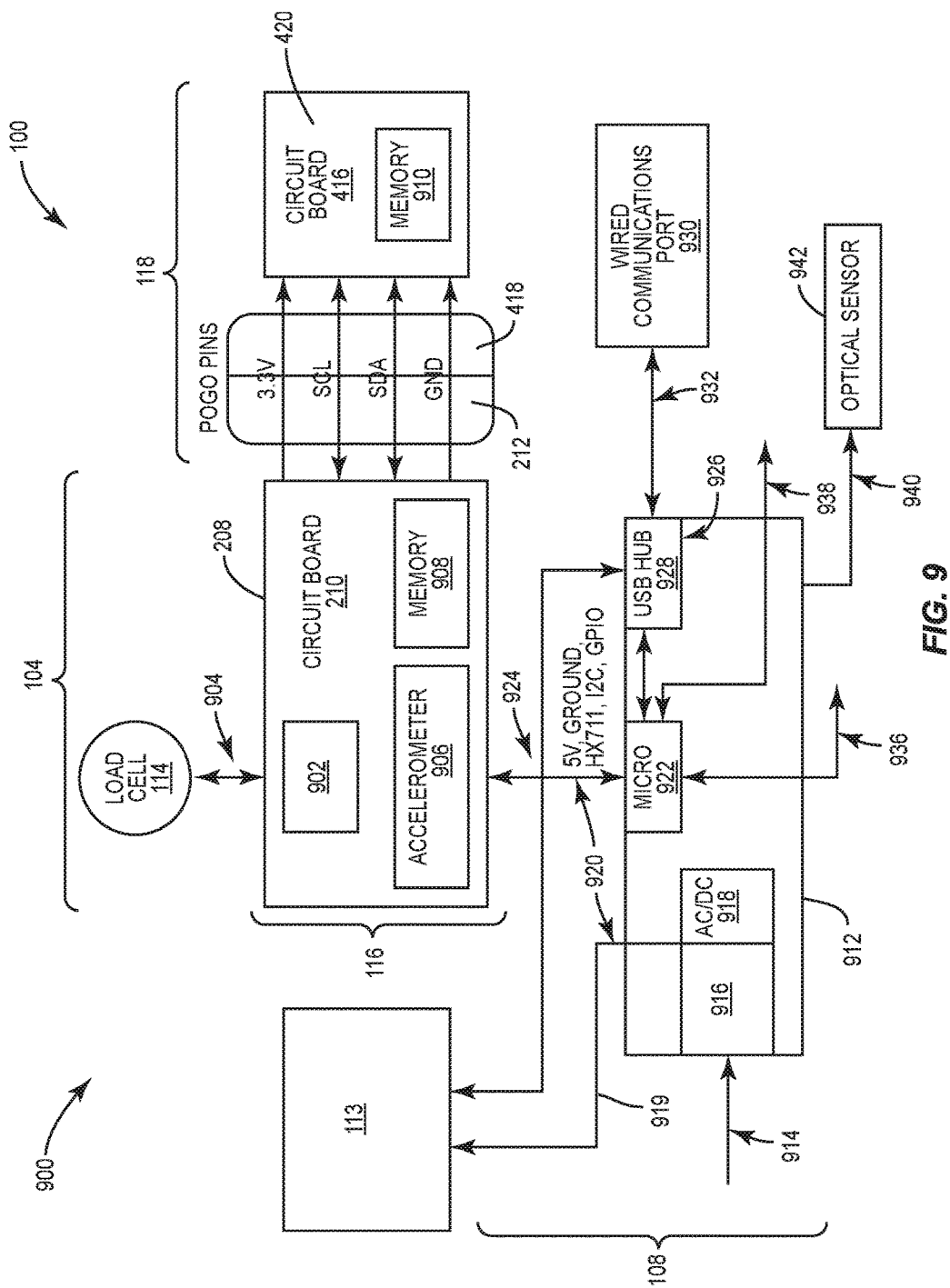
FIG. 9 is a block diagram of an exemplary electronic architecture of the fluid container measurement system in FIGS. 1A and 1B, including a measurement control circuit and electrical interfaces in the measurement control circuit, and a disposable member electrical circuit and disposable member electrical interface of the load cell linkage member.

With reference to FIG. 9, the measurement control circuit 208 in this example includes a microcontroller 902 configured to provide the control operations interfacing with the load cell 114 to receive electrical signals 904 used to measure a load on the load cell 114. The measurement control circuit 208 may also include an accelerometer 906 to detect the angle of mounting of the load measurement assembly 104, and in the example herein the base 108, relative to the support surface 110. Depending on the angle of mounting, the measurement control circuit 208 may or may not allow measurement of the fluid container 102. The measurement control circuit 208 also includes memory 908 for storing measurement data for load measurements on the load cell 114, and other data as will be discussed in more detail below. As discussed above, the measurement control circuit 208 includes the measurement electrical interface 212 that is configured to be electrically coupled to the disposable member electrical interface 418 as part of the load cell linkage member 118. The disposable member electrical interface 418 is electrically coupled to the disposable member electrical circuit 420 that includes memory 910 (e.g., EEPROM) configured to store data, such as an identification indicia (e.g., serial number), as will be discussed in more detail below.

With continuing reference to FIG. 9, a main circuit 912 may also be included in the fluid container measurement system 100, such as in the base 108, to receive alternating current (AC) power 914 for operation of the disposable member electrical circuit 420. The main circuit 912 may include a power input interface 916 configured to receive AC power 914 such as from a standard AC outlet. The main circuit 912 may include an AC to direct current (DC) converter 918 to convert the received AC power 914 into DC power 920. The DC power 920 may be provided over a communications bus 919 cabling to the display 113. The cabling may be run internal to the rails 112A, 112B of the fluid container measurement system 100. The DC power 920 may also be provided over cabling to the measurement control circuit 208, as shown in FIG. 9. The main circuit 912 may include a microprocessor 922 or other control circuit that is communicatively coupled over a communications bus 924 to the microcontroller 902 in the measurement control circuit 208. The communications bus 924 may extend from the base 108 inside the housing 200 of the load measurement assembly 104. The microprocessor 922 may include such functions as communicating received measurement data from the measurement control circuit 208 to the display 113 and to wireless and/or wired interfaces. For example, a wired interface circuit 926 in the form of a Universal Serial Bus (USB) hub 928 is provided in the main circuit 912 that is coupled to a wired communications port 930 over a communications bus 932. The main circuit 912 may also include a wired communication port 936, such as a RS-232 port and a footswitch accessor port 938 for footswitch control.

In certain embodiments, the main circuit 912 may include an optical sensor port 940 in communication with one or more optical sensors 942. In certain embodiments, such as those disclosed in FIGS. 17A-17D, each optical sensor 942 is configured to detect whether the tube 136 is properly positioned and/or supported in the load measurement assembly 104. For example, the optical sensor 942 may be a visible light optical sensor configured to detect a particular wavelength for detecting a particular color of tape positioned around the tube 136 to determine whether the tube 136 is properly positioned and/or supported within the load measurement assembly 104, as discussed in more detail in FIGS. 18A-18B below. As another example, the optical sensor 942 may be an infrared sensor that detects an object, such as tape positioned around the tube 136 by sensing the reflected infrared emission from the tape. This may be particularly advantageous when the support member is integrally formed with (e.g., non-removable from) the load measurement assembly 104. As another example, the optical sensor 942 may be configured to detect a bar code, a predefined ink composition, a predefined color, and/or a mechanical feature. In certain embodiments, other types of sensors could be used. As used herein, the term "sensor" includes a device that detects or measures a physical property and responds to the detection (e.g., optical sensors, mechanical switches, etc.). In certain embodiments, the sensor may include an optical sensor (e.g., laser proximity sensor), a mechanical switch, an ultrasonic sensor, an RFID (radio-frequency identification) sensor, capacitive sensor, resistive sensor, and/or force sensor (e.g., load cell), etc. In particular, for the force sensor, in certain embodiments, the force sensor may operate with the load cell 114, such that a predetermined length of tube may not be necessary (i.e., could work with any random tube length).

Figure 10:
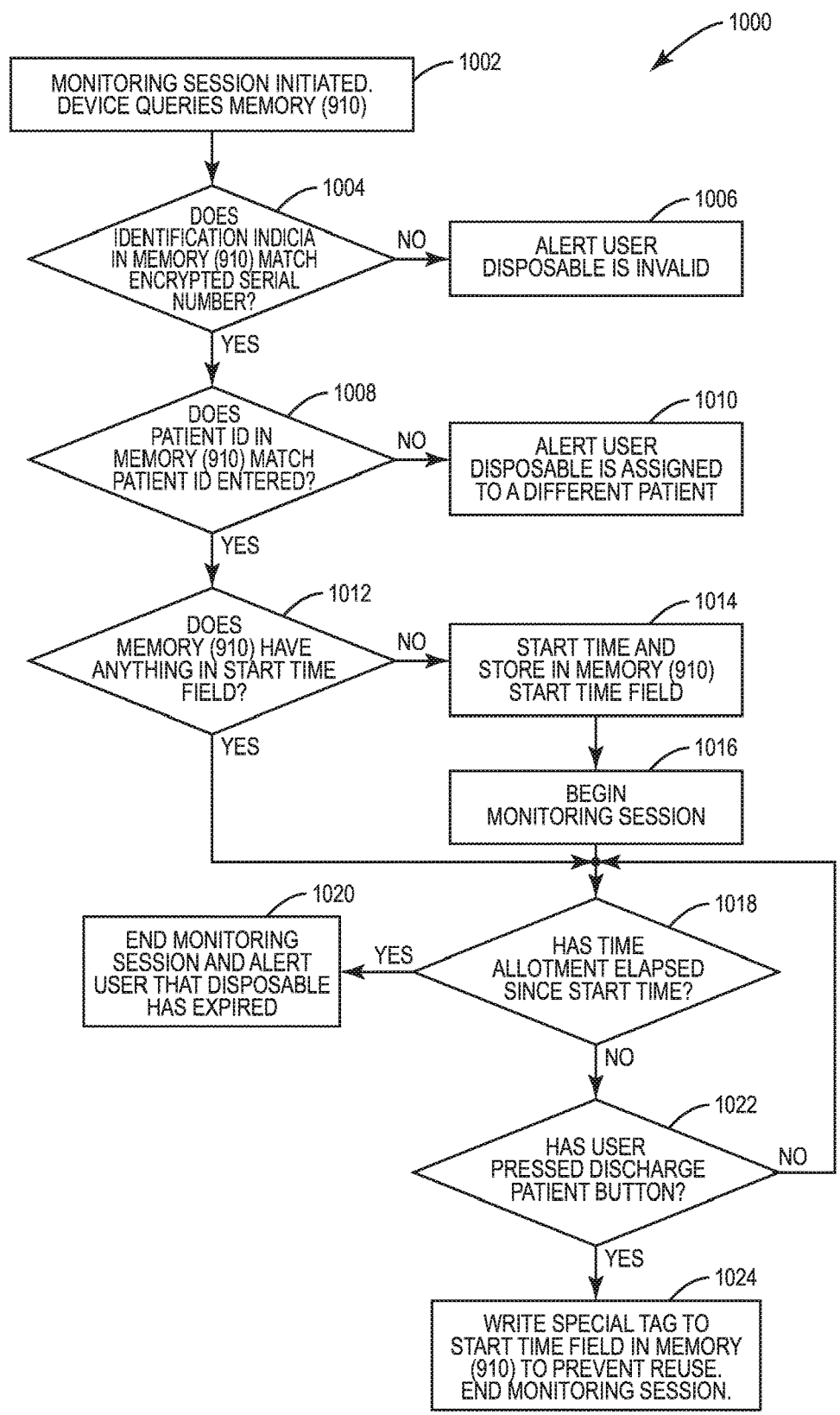
FIG. 10 is a flowchart illustrating an exemplary process of the measurement control circuit in the load measurement assembly of the fluid container measurement system in FIGS. 1A and 1B verifying an attached load cell linkage member and monitoring a load on the load cell from the attached load cell linkage member.
Figure 11:
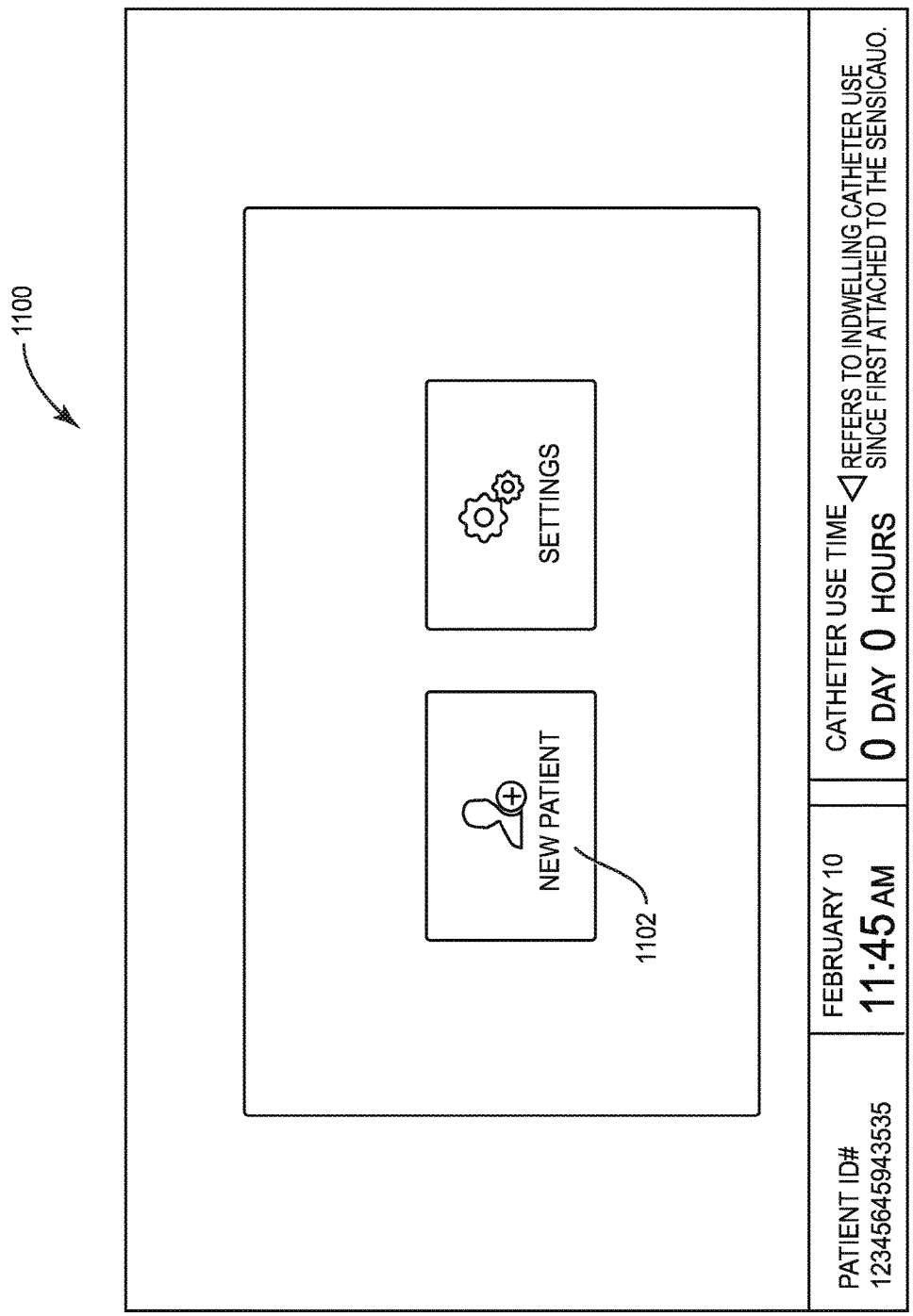
FIG. 11 is an exemplary graphical user interface (GUI) initialization screen displayed by the measurement control circuit on a display of the fluid container measurement system in FIGS. 1A and 1B.

FIG. 10 is a flowchart illustrating an exemplary process 1000 of an exemplary operation of the of the fluid container measurement system 100 in FIGS. 1A and 1B to measure a load on the load cell 114. In this regard, a monitoring session for the fluid container measurement system 100 is initiated by a user (block 1002). For example, the main circuit 912 in FIG. 9 may display a home GUI screen 1100 shown in FIG. 11 to prompt a user to initiate a monitoring session. For example, as shown in the home GUI screen 1100, a monitoring session may be initiated by a user selecting a "NEW PATIENT" button 1102. This causes the main circuit 912 to receive this user input over the communications bus 919 which in turn causes the main circuit 912 to send a message over the communications bus 924 to the measurement control circuit 208 in this example. In this example, as discussed above, the measurement control circuit 208 is configured to detect the presence of an installed load cell linkage member 118 by the coupling of the measurement electrical interface 212 with the disposable member electrical interface 418. As an example, the home GUI screen 1100 may not be displayed by the main circuit 912 on the display 113 until the measurement control circuit 208 is configured to detect the presence of an installed load cell linkage member 118 by the coupling of the measurement electrical interface 212 with the disposable member electrical interface 418 via communication over the communications bus 924.

With continuing reference to the exemplary process 1000 in FIG. 10, the measurement control circuit 208 is configured to detect the presence of an installed load cell linkage member 118 by the coupling of the measurement electrical interface 212 with the disposable member electrical interface 418. The measurement control circuit 208 queries an identification indicia stored in the memory 910 of the disposable member electrical circuit 420 in the load cell linkage member 118 (block 1002). The measurement control circuit 208 determines if the identification indicia stored in the memory 910 in the load cell linkage member 118 matches a serial number stored in the memory 908 of the measurement control circuit 208, which may be encrypted (block 1004). This check may be performed to determine if the load cell linkage member 118 is an authorized device attached to the load cell interconnect 116. If the identification indicia stored in the memory 910 in the load cell linkage member 118 does not match the serial number stored in memory 908 in this example (block 1004), the measurement control circuit 208 may cause an alert to be displayed on the display 113 to indicate that the load cell linkage member 118 is invalid and cannot be used for monitoring the load cell 114 (block 1006). However if the identification indicia stored in the memory 910 in the load cell linkage member 118 does match the serial number stored in memory 908 in this example (block 1004) such that the load cell linkage member 118 is valid and authorized, the measurement control circuit 208 may be configured to start the monitoring session or perform other verifications before beginning a monitoring session.

For example, the measurement control circuit 208 may be further configured to determine if a patient identification stored in the memory 910 of the load cell linkage member 118 matches a patient identification entered by a user through the display 113 and/or stored in the memory 908 (block 1008). If the load cell linkage member 118 was previously used to monitor a patient, a patient identification identifying the patient may be stored in the memory 910 of the load cell linkage member 118 so that the load cell linkage member 118 can be associated with that patient. If a patient identification stored in the memory 910 of the load cell linkage member 118 does not match a patient identifier entered by a user through the display 113 and/or stored in the memory 908 (block 1008), the measurement control circuit 208 may cause an alert to be displayed on the display 113 to indicate that the load cell linkage member 118 is assigned to a different patient and cannot be used for a monitoring session for the entered patient (block 1010). If a patient identifier stored in the memory 910 of the load cell linkage member 118 matches a patient identifier entered by a user through the display 113 and/or stored in the memory 908 (block 1008), the measurement control circuit 208 may go on to start the monitoring session or perform other verifications before beginning a monitoring session.

Figure 12:
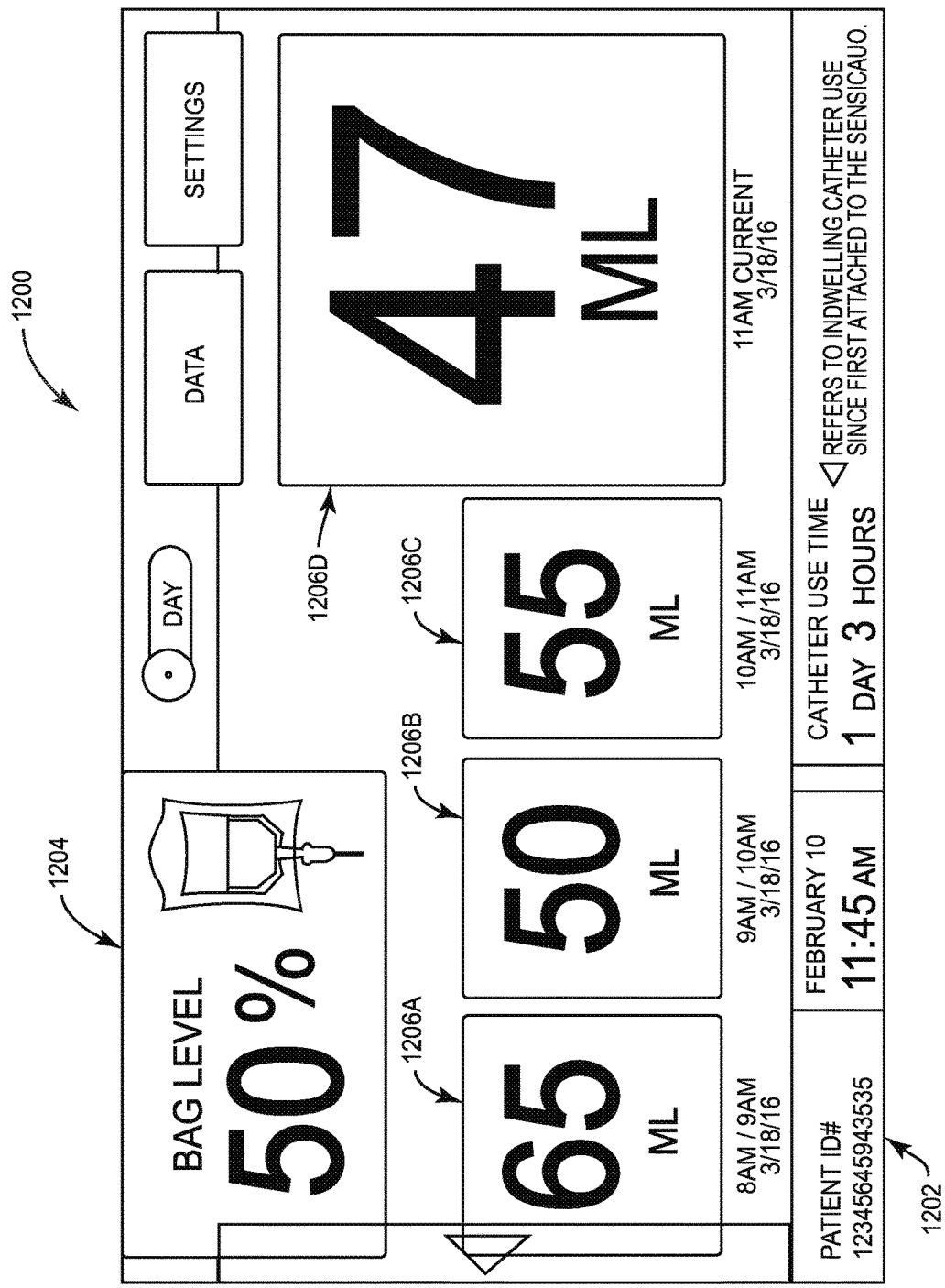
FIG. 12 is an exemplary GUI measurement screen displayed by the measurement control circuit on a display of the fluid container measurement system in FIG. 1A illustrating measurements made by the by the measurement control circuit based on a load disposed on the load cell from the attached load cell linkage member.

With continuing reference to FIG. 10, in this example, the measurement control circuit 208 may be further configured to determine if the memory 910 for the attached load cell linkage member 118 contains any information in a start time field therein (block 1012). If not, the measurement control circuit 208 may be further configured to start a timer and store the start time in a start time field in the memory 910 of the load cell linkage member 118 (block 1014). Either way, a monitoring session is next initiated (block 1016). The electrical signals 904 received by the measurement control circuit 208 from the load cell 114 are used to determine the weight of the fluid container 102 attached to the support member 120 of the load cell linkage member 118. For example, the monitored information may be displayed on the display 113 in a data GUI 1200 as shown in FIG. 12. As shown therein, the fluid container 102 level for a patient identifier 1202 may be displayed in a bag level area 1204. The weight or volume of the fluid container 102 over serially monitored periods of time is displayed in areas 1206A, 1206B, 1206C with the most current weight or volume measurement shown in larger area 1206D.

With continuing reference to FIG. 10, in this example, the measurement control circuit 208 determines if a time allotment has elapsed since the start time (block 1018). If so, the monitoring session is ended, and the measurement control circuit 208 causes an alert to be displayed on the display 113 to indicate to the user that the time limit for use of the load cell linkage member 118 has expired (block 1020). A new load cell linkage member 118 may need to be used for the patient if more monitoring is to be performed for the patient. If the measurement control circuit 208 determines that the time allotment elapsed since the start time has not expired (block 1018), then the measurement control circuit 208 continues monitoring of the load cell 114 until the measurement control circuit 208 determines if the user has pressed a discharge patient button (block 1022). In this case, the measurement control circuit 208 writes a special tag to the start time field in the memory 910 of the load cell linkage member 118 to prevent reuse of the load cell linkage member 118, and the monitoring session ends (block 1024).

The measurement control circuit 208 may also be configured to perform a calibration procedure before beginning a monitoring session of the load cell 114 to "zero out" the load cell 114. In this regard, the measurement control circuit 208 may be configured to measure a first load on the load cell 114 when the disposable member electrical interface 418 is not electrically coupled to the measurement electrical interface 212. The measurement control circuit 208 then stores the force/weight on the load cell 114 in the memory 908 of the measurement control circuit 208 as a calibration value. Then, when the measurement control circuit 208 detects that the disposable member electrical interface 418 is electrically coupled to the measurement electrical interface 212, meaning that a load cell linkage member 118 has been properly attached to the load cell interconnect 116, the measurement control circuit 208 measures a second load on the load cell 114 to monitor the load cell 114. The first load measurement as the calibration value can be subtracted from the monitored force on the load cell 114 when the load cell linkage member 118 is attached as a way to zero out or calibrate the load cell 114.

Figure 13A:
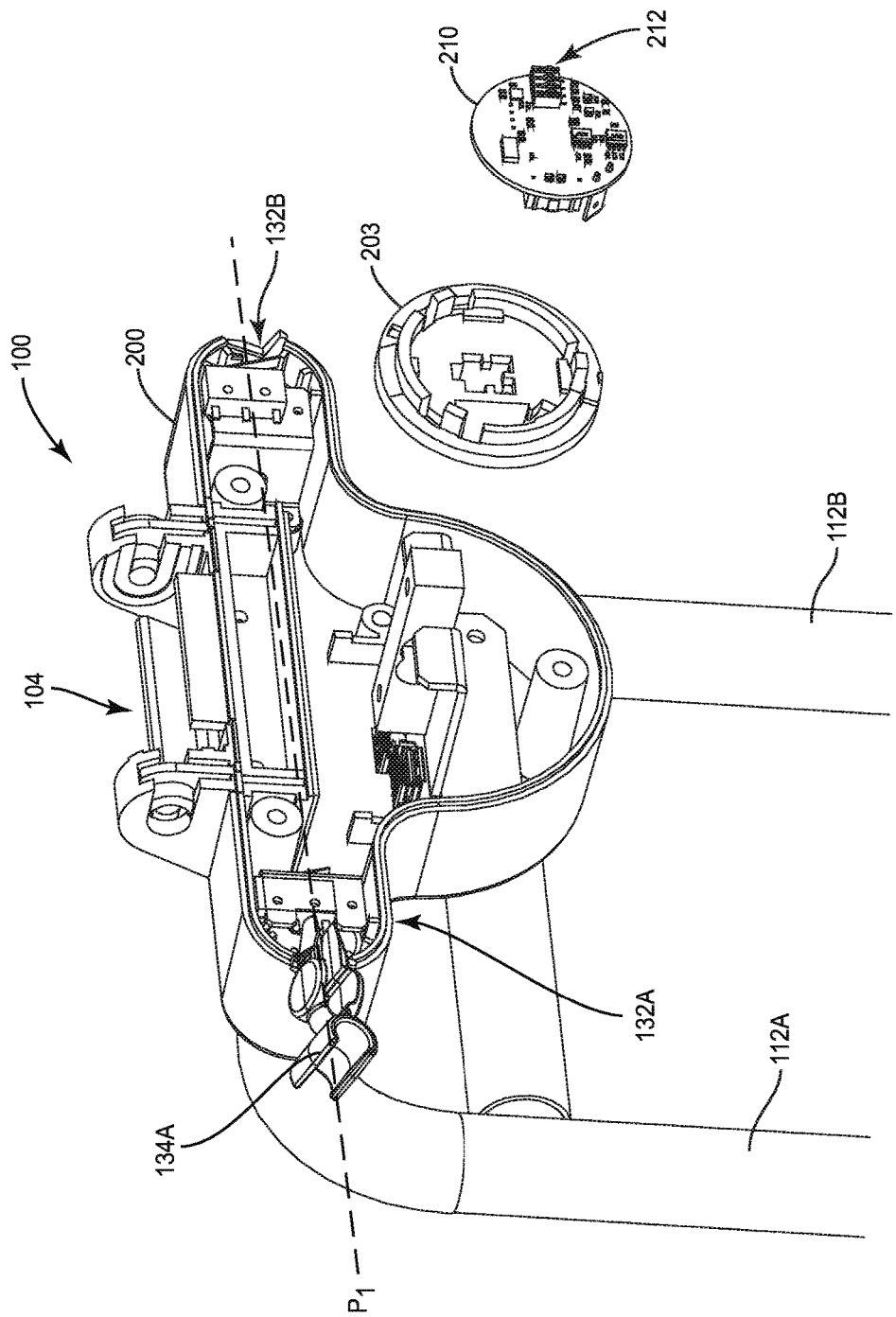
FIG. 13A is a close-up, side perspective view of an internal compartment of the load measurement assembly of the fluid container measurement system in FIGS. 1A and 1B, illustrating a tether support member interface configured to receive a tether support member for supporting a tube of a fluid container so that the load of the tube does not strain the load cell.
Figure 13B:
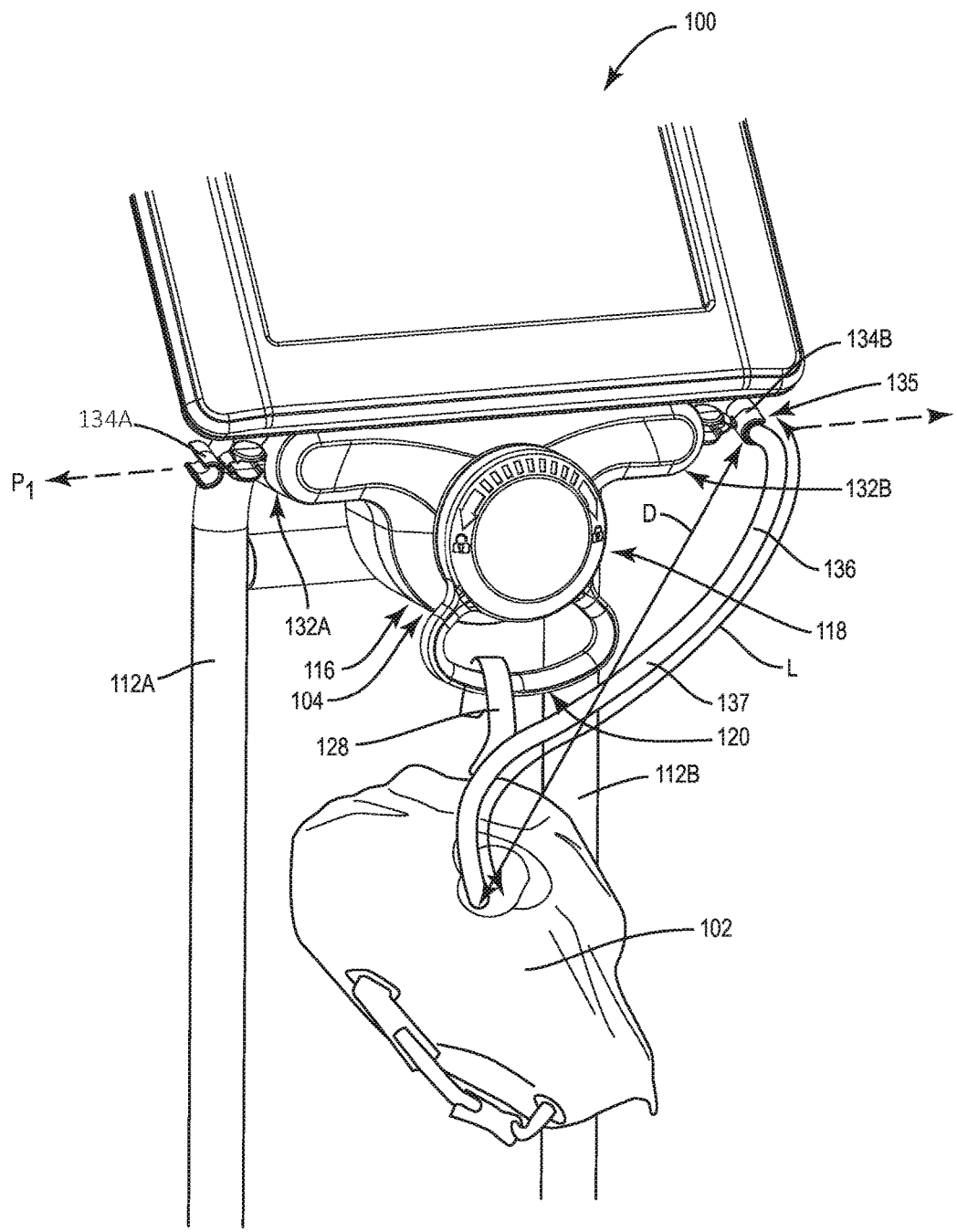
FIG. 13B is a close-up, side perspective view of a tube from a fluid container secured in a tether support member inserted into the tether support member interface of the load measurement assembly of the fluid container measurement system in FIGS. 1A and 1B with the fluid container attached to the tether support member of a load cell linkage member.

FIG. 13A is a close-up, side perspective view of the housing 200 of the load measurement assembly 104 to further illustrate the tether support member interfaces 132A, 132B. As discussed above, the tether support member interfaces 132A, 132B are each configured to receive the tether support members 134A, 134B, respectively, for supporting the tube 136 of the fluid container 102, as shown in FIG. 13B. As shown in FIGS. 13A and 13B, the load measurement assembly 104 includes the tether support member interfaces 132A, 132B disposed in a plane $P_1$ above the load cell interconnect 116. The tether support member interfaces 132A, 132B are configured to receive the tether support members 134A, 134B configured to support the tube 136 from the fluid container 102.

As shown in FIG. 13B, the tether support members 134A, 134B are configured to support the tube 136 of the fluid container 102 in the support area 135 of the tube 136 with the load measurement assembly 104. This allows a predefined length L of the tube 136 to form the supported portion 137 of the tube 136 to be supported by the support member 120 as part of the weight of the fluid container 102. The weight of the supported portion 137 of the tube 136 and the fluid container 102 can also be calibrated during a calibration procedure, as will be discussed in more detail below, so that the weight of the fluid container 102 and the supported portion 137 of the tube 136 is not part of the fluid measurement. Further, the predefined length L of the supported portion 137 of the tube 136 can be selected to provide slack in the supported portion 137 of the tube 136 when supported by the tether support member 134, so that a strain is avoided in the supported portion 137 of the tube 136. Thus, a force from the load measurement assembly 104 is not imparted on the fluid container 102 from strain. Further, in this example, the tether support member 134B supports the tube 136 connected to the fluid container 102 such that the tube 136 is supported in the support area 135 and does not slide or rotate relative to the tether support member 134B.

The tube 136 may have a marking to indicate the position of the support area 135 in which the tube 136 is to be inserted into the tether support member 134B to control the predefined length L of the supported portion 137 of the tube 136 located between the tether support member 134B and the hook 128. The length L of the supported portion 137 of the tube 136 is based on the distance between the tether support member 134A, 134B and the support member 120. If this length of the supported portion 137 of the tube 136 is too short, a strain force will be imposed on the support portion 137 of the tube 136. This will cause a force from the load measurement assembly 104 to be imposed on the support portion 137 of the tube 136 and thus also the fluid container 102, which will unduly influence the force on the support member 120 and thus the load cell 114. Further, the tether support members 134A, 134B are designed such that a supported portion 137 of the tube 136 will be angled upward so that any fluid contained in the tube 136 is not pooled inside the tube 136 and will be more easily drained to the fluid container 102.

The tether support member 134 may include an electrical interface that is configured to be electrically coupled to the measurement control circuit 208 when the tether support member 134 is installed in the tether support member interface 132. When inserted into a respective tether support member interface 132A, 132B, the tether support member 134A, 134B may be electrically coupled to the measurement control circuit 208. In this manner, the measurement control circuit 208 can be configured to detect a tether support member 134A, 134B inserted into a respective tether support member interface 132A, 132B. The measurement control circuit 208 may be configured to measure a load on the load cell 114 based on the received electrical signals 904 from the load cell 114, if the tether support member 134A, 134B is detected as being inserted into the tether support member interface 132A, 132B. The measurement control circuit 208 may be configured to not measure a load on the load cell 114 based on the received electrical signals 904 from the load cell 114, if the tether support member 134A, 134B is not detected as being inserted into a tether support member interface 132A, 132B. The measurement control circuit 208 may also be further configured to detect sudden changes in force on the load cell 114 as an indication that a tube 136 may have been removed from a tether support member 134 when the tether support member 134 was previously detected. In response, the measurement control circuit 208 can be configured to re-calibrate the load cell 114 when the tube 136 is reattached to the tether support member 134.

Figure 14:
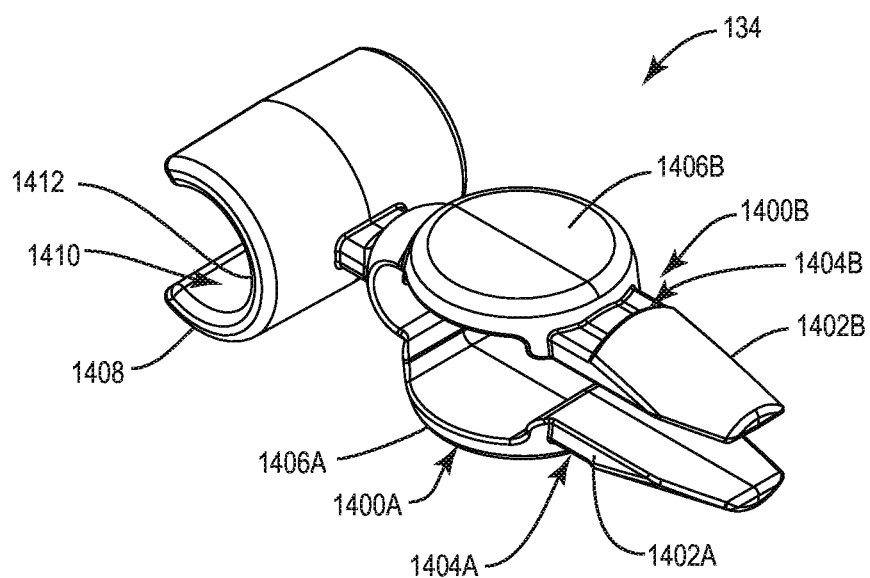
FIG. 14 is a side perspective view of an exemplary tether support member configured to be inserted into a tether support member interface of the load measurement assembly of the fluid container measurement system in FIGS. 1A and 1B and support a tube of a fluid container attached to the tether support member of a load cell linkage member.

FIG. 14 is a side perspective view of an exemplary tether support member 134 configured to be inserted into a tether support member interface 132 of the load measurement assembly 104 of the fluid container measurement system 100 in FIGS. 1A and 1B, and support a tube 136 of a fluid container 102 attached to a load cell linkage member 118. FIGS. 15A-15D are front, top and bottom, right side, and left side views, respectively, of the tether support member 134 in FIG. 14. In this regard, the tether support member 134 includes an opposing pair of cantilevered arms 1400A, 1400B each including an inward biased member 1402A, 1402B configured to be inserted into the tether support member interface 132. The cantilevered arms 1400A, 1400B are bent inward to each other as the inward biased members 1402A, 1402B pass through the tether support member interface 132. The inward biased members 1402A, 1402B each contain shoulders 1404A, 1404B such that the tether support member 134 cannot be removed from of the tether support member interface 132 unless the opposing pair of cantilevered arms are squeezed inward to allow the inward biased members 1402A, 1402B to clear and not interfere with the tether support member interface 132. A pair of platforms 1406A, 1406B are provided to allow the cantilevered arms 1400A, 1400B to be bent inward with fingers. A slot member 1408 is attached to the cantilevered arms 1400A, 1400B and contains an opening 1410 and semi-circular inside surface 1412 to support the tube 136. The semi-circular inside surface 1412 may be prepared such that the tube 136 will not slip therein.

A means may be provided with which the tether support member 134 supports the tube 136 such that a desired length of the tube 136 from the fluid container 102 is supported by the tether support member 134. This could be a measurement scale on the package, a tool attached to the tether support member 134, and/or additional plastic parts added to the tether support member 134 that wrap around and set distance without torqueing the tube 136. Additionally, a custom fluid container 102 and tube set with a custom manufacturing-affixed permanent tether support member 134 that was always applied at the correct distance for a particular tube 136 diameter/thickness ratio could be provided. This could be provided through overmolding, heat bonding, or other permanent mechanical attachments.

As discussed above, the tether support member 134 is configured to support the tube 136 of the fluid container 102 in the support area 135 of the tube 136 with the load measurement assembly 104. This allows a predefined length L of the supported portion 137 of the tube 136 to be supported by the support member 120 as part of the weight of the fluid container 102. The weight of the supported portion 137 of the tube 136 and the fluid container 102 can also be calibrated during the above discussed calibration procedure so that the weight of the fluid container 102 and the supported portion 137 of the tube 136 is not part of the fluid measurement. Further, the predefined length L of the supported portion 137 of the tube 136 can be selected to provide slack in the supported portion 137 of the tube 136 when supported by the tether support member 134, so that a strain is reduced or avoided in the supported portion 137 of the tube 136. Thus, a force from the load measurement assembly 104 is not imparted on the fluid container 102 from strain.

Figure 16:
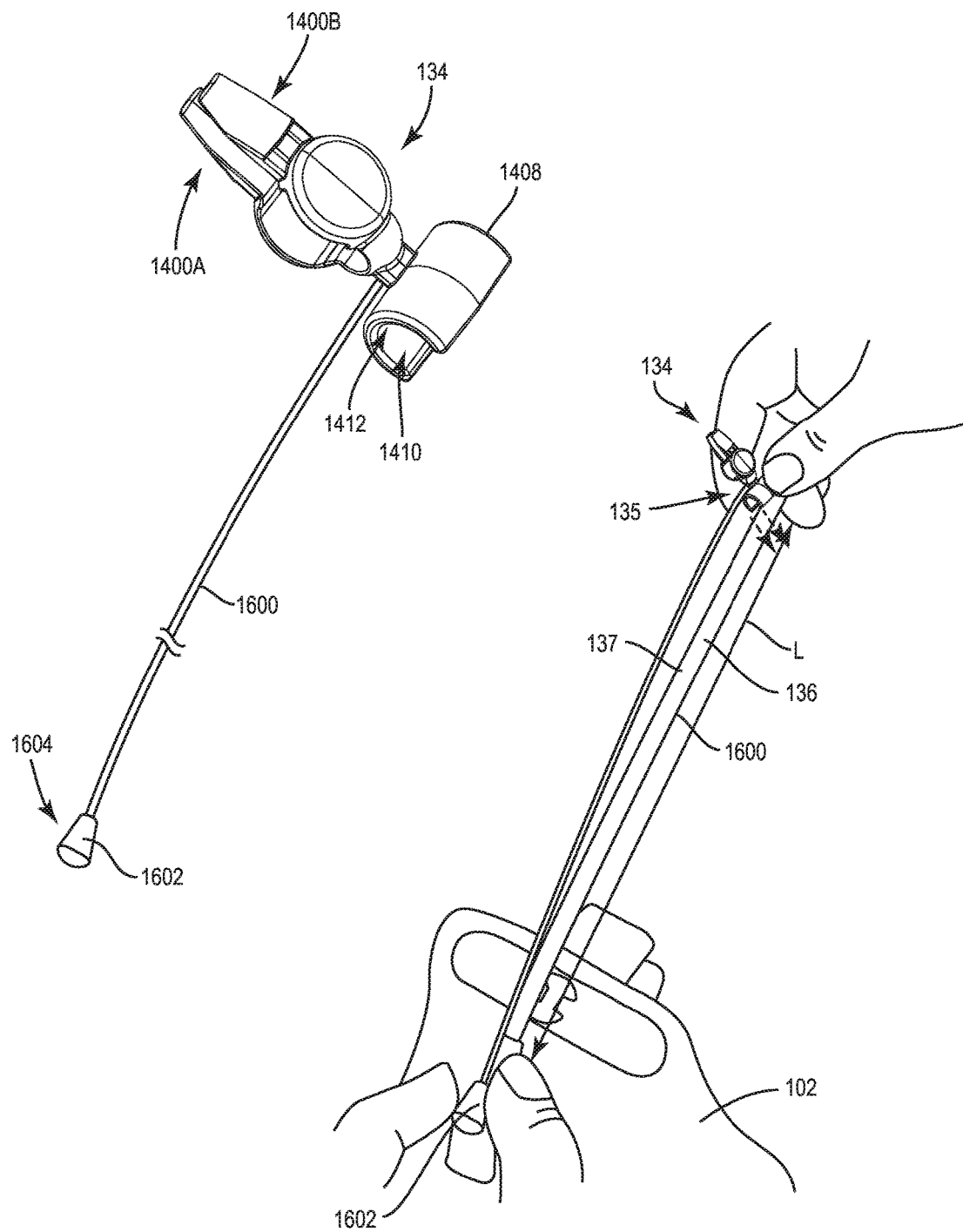
FIG. 16 is side perspective view of the tether support member in FIGS. 15A-15D that includes an additional optional integrated measuring string to assist in measuring the length of the tube extending from a fluid container to determine the attachment location of the tether support member to the tube to prepare the tether support member to be received in the tether support member interface of the fluid container measurement system in FIGS. 1A and 1B.

It may be desired to provide a convenient method for a user to determine the support area 135 to be inserted into the tether support member 134 to provide the desired length L of the tube 136 as the supported portion 137 between the tether support member 134 and the support member 120 of the load cell linkage member 118. In this regard, FIG. 16 is a side perspective view of the tether support member 134 in FIGS. 15A-15D that includes an additional optional integrated measuring string 1600. The measuring string 1660 is attached to the tether support member 134 as shown, and thus is integrated with the tether support member 134. The measuring string 1600 assists in measuring the length L of the tube 136 extending from the fluid container 102 to determine the support area 135 of the tether support member 134 to the tube 136 to prepare the tether support member 134 to receive the tube 136. An end portion 1602 is provided on a distal end 1604 of the measuring string 1600 to allow a user to easily pull on and manipulate the measuring string 1600 to measure against the tube 136, as shown in FIG. 16. The tether support member 134 can then be inserted in the tether support member interface 132 of the fluid container measurement system 100 in FIGS. 1A and 1B such that the load measurement assembly 104 supports the supported portion 137 of the tube 136.

Figure 17A:
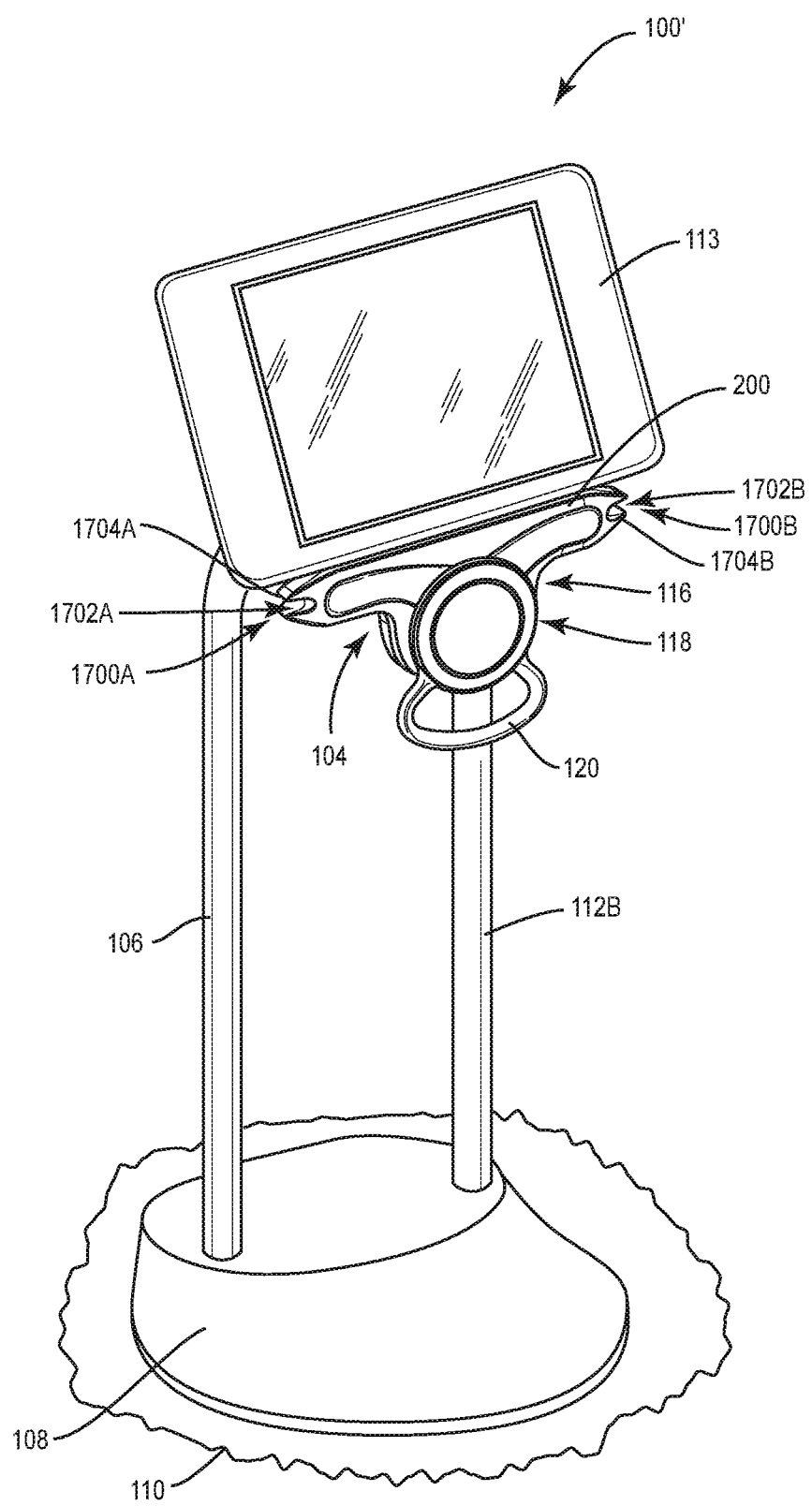
FIG. 17A is a side perspective view of an alternative fluid container measurement system that includes a load measurement assembly that includes integrated strain reliefs as opposed to tether support member interfaces for securing a tube of a fluid container attached to a tether support member of a load cell linkage member.

FIG. 17A is a side perspective view of an alternative fluid container measurement system 100' that includes the same components as that in the fluid container measurement system 100 in FIGS. 1A and 1B. Common components are shown between the alternative fluid container measurement system 100' in FIG. 17A and the fluid container measurement system 100 in FIGS. 1A and 1B. In the alternative fluid container measurement system 100' in FIG. 17, an alternative tube strain relief for a tube of a fluid container supported by the load cell linkage member 118 is provided. In this regard, the housing 200 of the load measurement assembly 104 includes integrated strain reliefs 1700A, 1700B. The integrated strain reliefs 1700A, 1700B include slot members 1702A, 1702B that include semi-circular inside surfaces 1704A, 1704B similar to the slot member 1408 in the tether support member 134 in FIGS. 14-15D. The slot members 1702A, 1702B operate similarly to the slot member 1408 of the tether support member 134.

Figure 17B:
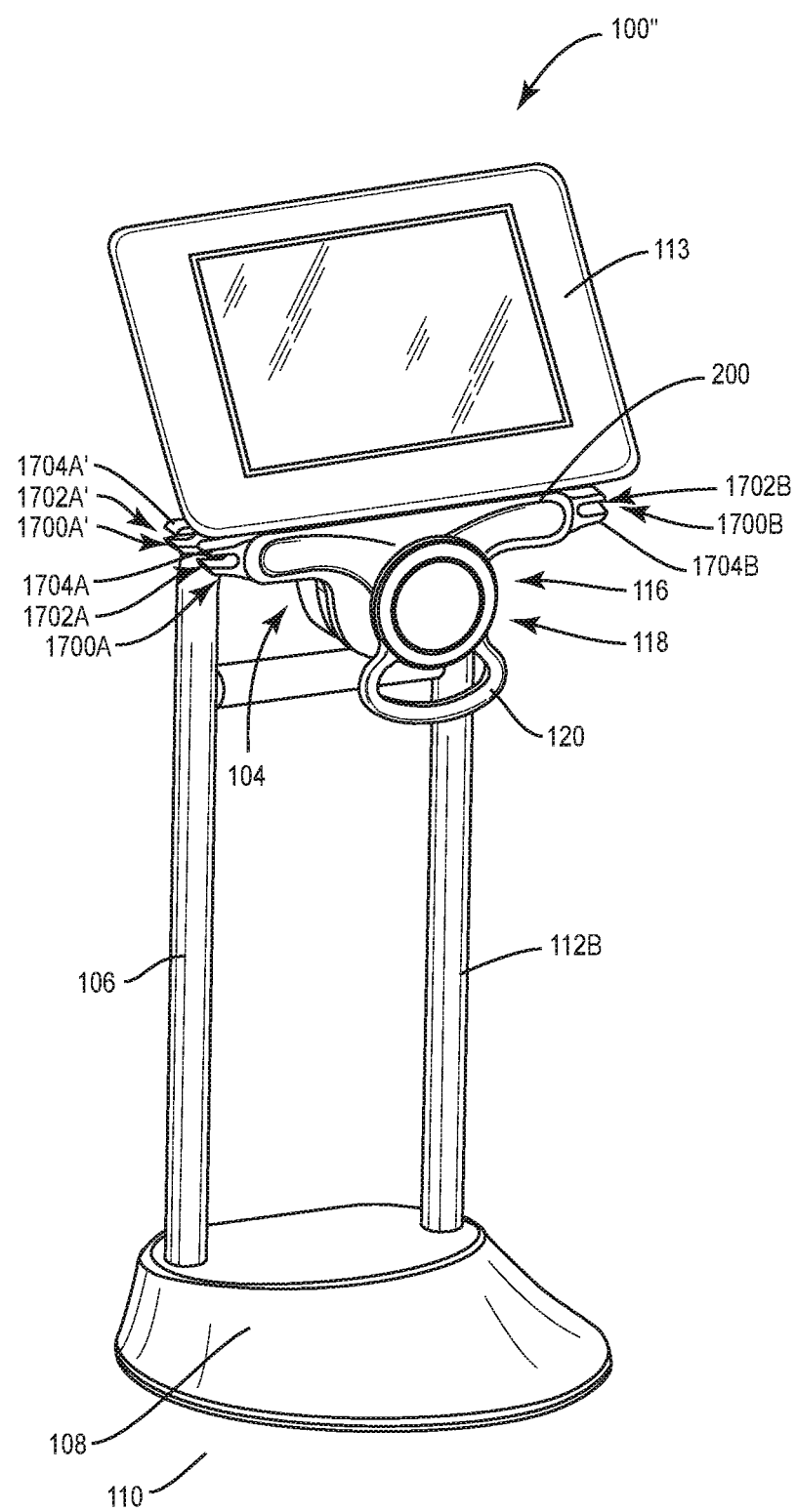
FIG. 17B is a side perspective view of another alternative fluid container measurement system that includes a load measurement assembly that includes a first and second set of integrated strain reliefs for securing a tube of a fluid container attached to a load cell linkage member.
Figure 17C:
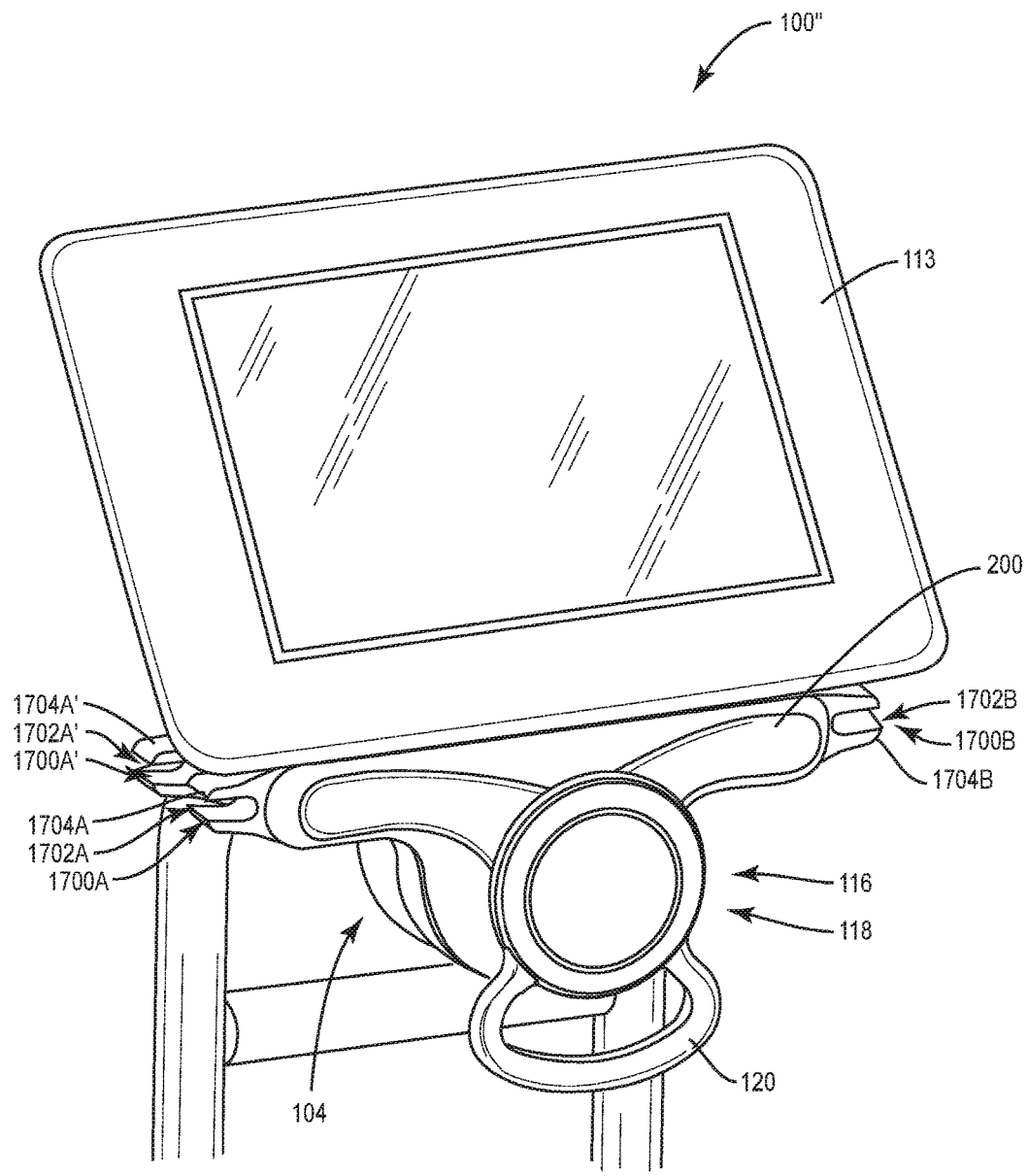
FIG. 17C is a close up side perspective view of the alternative fluid container measurement system of FIG. 17B.

FIGS. 17B-17C are views of another alternative fluid container measurement system 100" that provides an alternative tube strain relief for a tube of a fluid container supported by the load cell linkage member 118 to mount a portion of the tube 136 for use with an optical sensor 942. Common components are shown between the alternative fluid container measurement system 100" in FIG. 17B and the fluid container measurement system 100 in FIGS. 1A and 1B and the fluid container measurement system 100' of FIG. 17A, and thus will not be re-described.

As shown in FIG. 17B, in the alternative fluid container measurement system 100" the housing 200 of the load measurement assembly 104 includes a first set of integrated strain reliefs 1700A, 1700B. The integrated strain reliefs 1700A, 1700B include slot members 1702A, 1702B that include semi-circular inside surfaces 1704A, 1704B similar to the slot member 1408 in the tether support member 134 in FIGS. 14-15D. The slot members 1702A, 1702B operate similarly to the tether support member 134. Further, the housing 200 of the load measurement assembly 104 includes a second set of integrated strain reliefs 1700A', 1700B' that include semi-circular inside surfaces 1704A', 1704B' similar to the slot member 1408 in the tether support member 134 in FIGS. 14-15D. The slot members 1702A', 1702B' operate similarly to the slot member 1408 of the tether support member 134. The second set of integrated strain reliefs 1700A', 1700B' are aligned with and positioned behind, respectively, the first set of integrated strain reliefs 1700A, 1700B. The tether support member 134, as described above, includes a mechanical feature (e.g., cantilevered arms 1400A, 1400B and inward biased member 1402A, 1402B) configured to be inserted into the tether support member interface 132, such that the measurement control circuit 208 can detect a tether support member 134A, 134B inserted into a respective tether support member interface 132A, 132B. Comparatively, the fluid container measurement systems 100', 100" include an optical sensor 942 to detect whether the tube 136 is properly installed, as explained below in more detail.

Figure 17D:
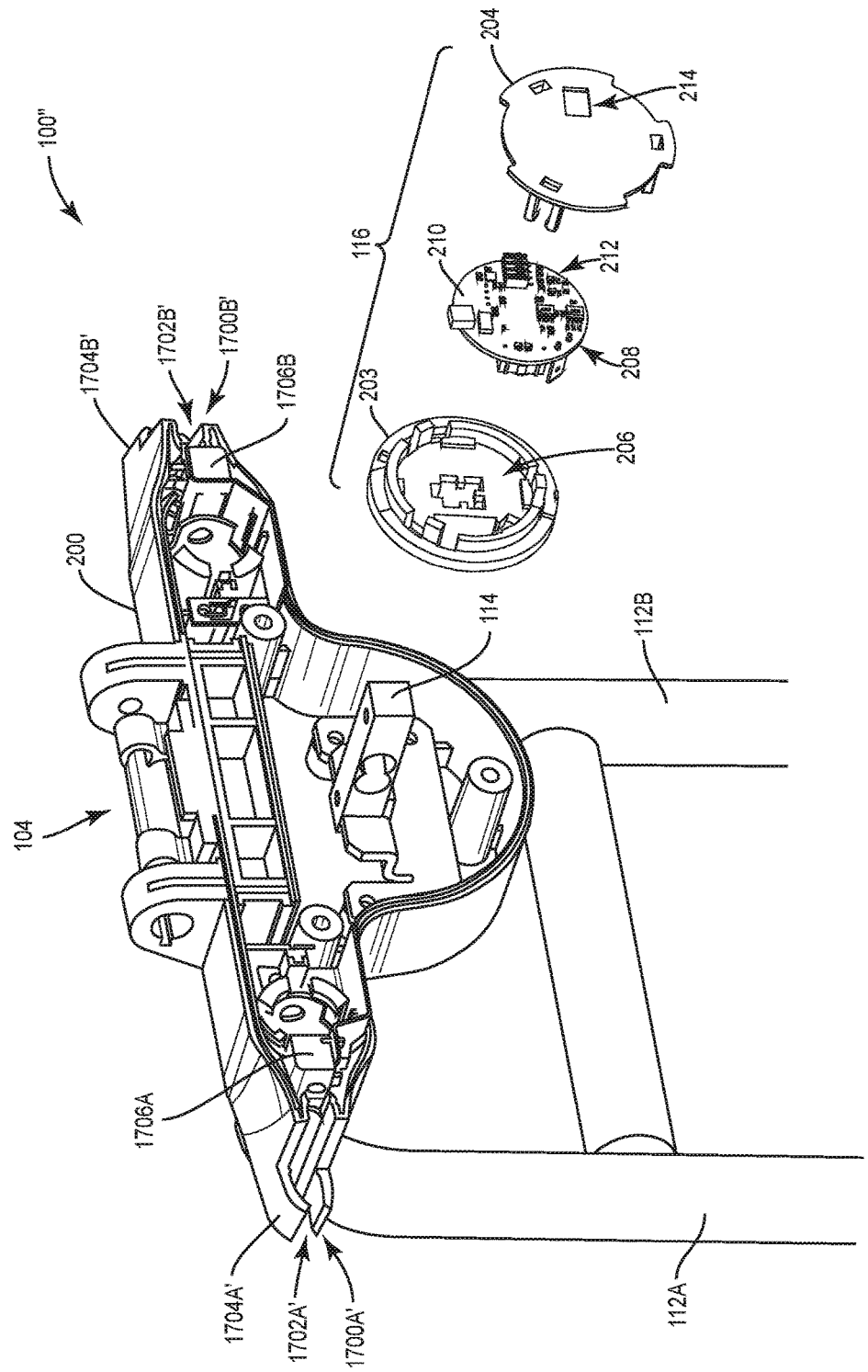
FIG. 17D is an exploded, side perspective view of an internal compartment of the load measurement assembly of the fluid container measurement system in FIGS. 17B-17C, illustrating first and second optical sensors for detecting whether the tube is properly positioned and secured within the first or second sets of integrated strain reliefs.

As shown in FIG. 17D, the load measurement assembly 104 includes a housing 200. The housing 200 contains the load cell 114 and other components, and provides a support mechanism to support the load measurement assembly 104 on the rails 112A, 112B. The load cell 114 is configured to provide electrical signals to the measurement control circuit 208 that can then be used to determine the force applied to the load cell 114 and thus the weight of the fluid container 102 attached to the load cell linkage member 118, as shown in FIG. 1A.

The load cell interconnect 116 is provided by a load cell interconnect shell 203 and a load cell interconnect interface 204 forming an interconnect cavity 206 therein. The load measurement assembly 104 also includes a measurement control circuit 208 as part of the load cell interconnect 116. The measurement control circuit 208 is electrically coupled to the load cell 114 and is configured to receive electrical signals from the load cell 114 indicative of the force imposed on the load cell interconnect 116. The measurement control circuit 208 is disposed on a circuit board 210 (e.g., a printed circuit board (PCB)) secured inside the interconnect cavity 206 of the load cell interconnect 116 in this example. The circuit board 210 also includes a measurement electrical interface 212 that is electrically coupled to the measurement control circuit 208 on the circuit board 210. The load cell interconnect interface 204 includes an opening 214 such that the measurement electrical interface 212 is aligned with the opening 214 and exposed therethrough when the load cell interconnect 116 is fully assembled. As will be discussed in more detail below, the exposed measurement electrical interface 212 is configured to be electrically coupled to a member electrical interface in the load cell linkage member 118 when the load cell linkage member 118 is secured to the load cell interconnect 116 in a measurement position.

The load measurement assembly 104 further includes an optical sensor 942 embodied as a first optical sensor 1706A and a second optical sensor 1706B. The first and second optical sensors 1706A, 1706B detect whether a tube 136 is properly positioned within the fluid container measurement system 100". Accordingly, the fluid container measurement system 100" is configured to alert a user if the tube 136 is not properly attached, if the tube 136 has been removed, etc. Further, the fluid container measurement system 100" can adjust or pause load cell measurements based on the information received from the first and second optical sensors 1706A, 1706B. The measurement control circuit 208 may be configured to measure a load on the load cell 114 based on the received electrical signals 904 from the load cell 114, if the tube 136 is detected by the first and/or second optical sensor 1706A, 1706B as being inserted into the first set of integrated strain reliefs 1700A, 1700B and/or the second set of integrated strain reliefs 1700A', 1700B'. The measurement control circuit 208 may be configured to not measure a load on the load cell 114 based on the received electrical signals 904 from the load cell 114, if the tube 136 is detected by the first and/or second optical sensor 1706A, 1706B as being inserted into the first set of integrated strain reliefs 1700A, 1700B and/or the second set of integrated strain reliefs 1700A', 1700B'. The measurement control circuit 208 may also be further configured to detect sudden changes in force on the load cell 114 as an indication that a tube 136 may have been removed from the first set of integrated strain reliefs 1700A, 1700B and/or the second set of integrated strain reliefs 1700A', 1700B' when the tube 136 was previously detected. In response, the measurement control circuit 208 can be configured to re-calibrate the load cell 114 when the tube 136 is reattached to the first set of integrated strain reliefs 1700A, 1700B and/or the second set of integrated strain reliefs 1700A', 1700B'. Compared to the tether support member 134, the first and second optical sensors 1706A, 1706B do not require an additional mechanical component, which may simplify use of the fluid container measurement system 100" and/or prevent misplacement or loss of such mechanical components, among other advantages.

The first optical sensor is positioned proximate to and between integrated strain relief 1700A and strain relief 1700A', and the second optical sensor 1706B is positioned proximate to and between integrated strain relief 1700B and strain relief 1700B'. As discussed above, the first optical sensor 1706A is used to detect whether a tube 136 is positioned within strain relief 1700A and/or strain relief 1700A', and similarly, the second optical sensor 1706B is used to detect whether a tube 136 is positioned within strain relief 1700B and/or strain relief 1700B'. In certain embodiments, the first and second optical sensors 1706A, 1706B are color optical sensors and detect a colored tape (e.g., white tape) positioned on the tube 136. Accordingly, the first and second sets of strain reliefs 1700A, 1700A', 1700B, 1700B' mount the tube 136 so that at least a portion of the tube 136 is reliably and repeatedly positioned in front of the first and second optical sensors 1706A, 1706B. Further, the first and second sets of strain reliefs 1700A, 1700A', 1700B, 1700B' provide a visual cue to an operator as to where the taped portion of the tube 136 must be placed.

It is noted that the strain reliefs discussed above may be attached to the housing 200 (see, e.g., FIGS. 1A-2B, 4A-4B, 6-8, 13A-15D), integrally attached to the housing 200 (see, e.g., FIGS. 17A-17D), and/or unattached and separate from the housing 200 (e.g., attached to a bedframe).

Figure 18A:
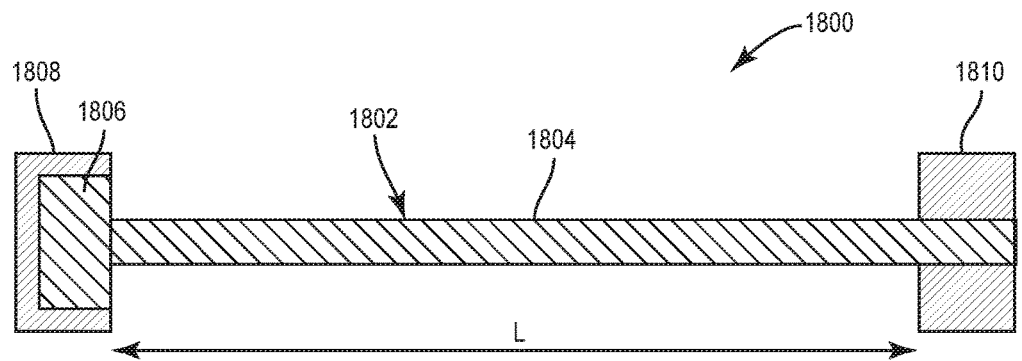
FIG. 18A is a top view of an optic ribbon assembly for placement on a tube to facilitate detection of the tube by the first or second optical sensors of FIG. 17D.
Figure 18B:
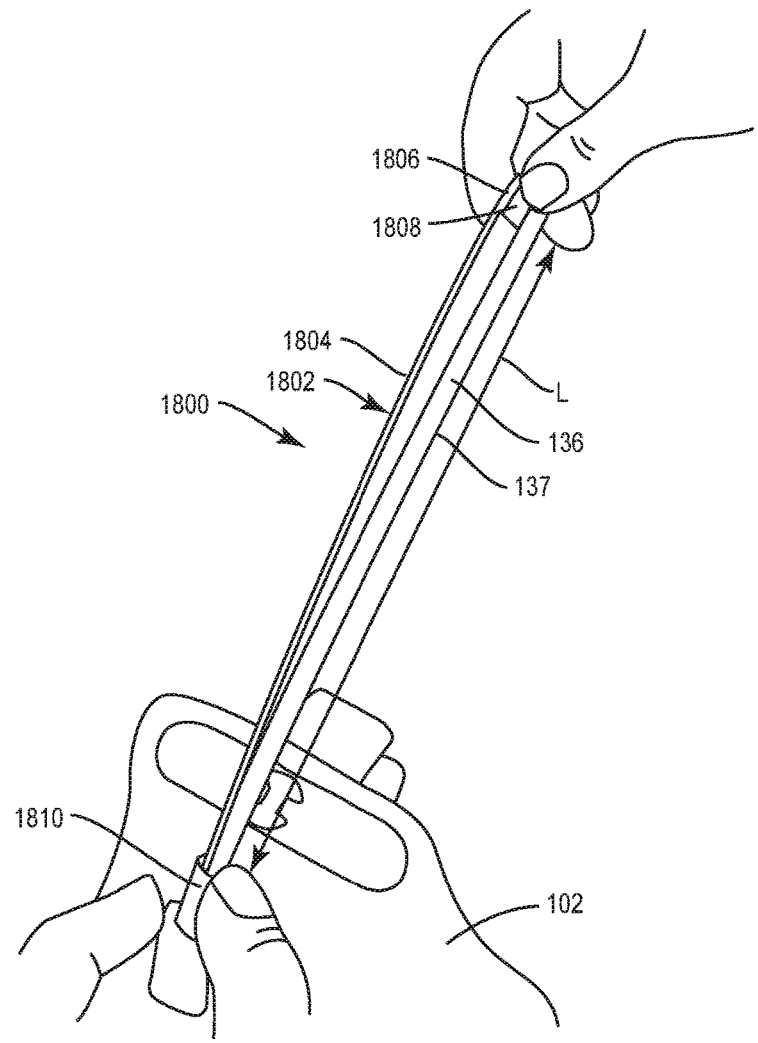
FIG. 18B is a side perspective view of application of the optic ribbon assembly of FIG. 18A to a tube to facilitate detection of the tube by the first and second optical sensors of FIG. 17D.

FIGS. 18A-18B are views of an indicator (e.g., an optical indicator) embodied as an optic ribbon assembly 1800 for placement on the tube 136 for detection by an optical sensor 942, as discussed above. The optic ribbon assembly 1800 includes an optic ribbon 1802 including a body 1804 and a head 1806 at one end of the body 1804, together forming a general T-shape. The head 1806 provides material for detection by the optical sensor 942. This is because the tube 136 may be clear, and the optical sensor 942 may have difficulty sensing a clear tube 136. The body 1804 has a predetermined length (L) for positioning the head 1806 of the optic ribbon 1802 on the tube 136. To facilitate detection by the optic sensor 942, in certain embodiments, the optic ribbon 1802 is opaque and/or one or more predefined colors (e.g., white). The optic ribbon assembly 1800 further includes a first tape strip 1808 at the head 1806 and a second tape strip 1810 at an end of the body 1804 opposite the head 1806. The first tape strip 1808 affixes the head 1806 of the optic ribbon 1802 at the appropriate location on the tube 136 and the second tape strip 1810 is to affix the end of the body opposite the head 1806 at an end of the tube 136 to facilitate placement of the head 1806, as explained below in more detail.

Referring to FIG. 18B, a user first positions the second tape strip 1810 at an end of the tube 136. The user is then able to use the length of the body 1804 of the optic ribbon 1802 to measure the length L of the tube 136 extending from the fluid container 102 to determine the appropriate placement of the head 1806 of the optic ribbon 1802 for detection by the optical sensor 942. Once the head 1806 is appropriately positioned on the tube 136, the head 1806 is affixed to the tube 136 by the first tape strip 1808. For example, the head 1806 of the optic ribbon 1802 can then be positioned between strain relief 1700A and strain relief 1700A' of the fluid container measurement system 100" of FIGS. 17B-17D for detection by the first optical sensor 1706A.

In other embodiments, the indicator includes a bar code, a predefined ink composition, a predefined color, and/or a mechanical feature (such as when working with an optical sensor 942, 1706A, 1706B). Accordingly, in certain embodiments, an optical sensor 942, 1706A, 1706B (or other type of sensor) may be configured to detect a bar code, a predefined ink composition, a predefined color, and/or a mechanical feature of the indicator (e.g., optical indicator or optical ribbon assembly 1800). In other embodiments, the indicator includes (additionally or alternatively) a mechanical actuator (e.g., the tube itself) for use with a mechanical switch, an ultrasonic reflector (e.g., the tube itself) for us with an ultrasonic sensor, an RFID tag for use with an RFID sensor, a capacitive element (e.g., the tube itself, a metallic tape, etc.) for use with the capacitive sensor, a resistive element (e.g., a metallic tape) for use with a resistive sensor, and/or force element (e.g., the weight of the tube itself).

As noted above, in certain embodiments, the indicator (e.g., optic indicator or optical ribbon assembly 1800) is positioned on the tube 136 at a predetermined length from the fluid container 102 for detection by an optical sensor 942 (or other type of sensor) of a fluid container measurement system 100, 100', 100" to ensure that the tube is tethered at the correct distance (e.g., to avoid undue influence of strain in the tube 136 and/or accurately account for the weight of the tube 136 in the weight measurement of the fluid container 102). Further, the indicator (e.g., optic indicator or optical ribbon assembly 1800) may be used to prevent use of an unauthorized fluid container assembly (e.g., fluid container 102) with the fluid container measurement system 100, 100', 100", where the fluid container assembly may include a fluid container 102, a tube 136, and/or an indicator (e.g., optic indicator or optical ribbon assembly 1800) on the tube 136.

Figure 19:
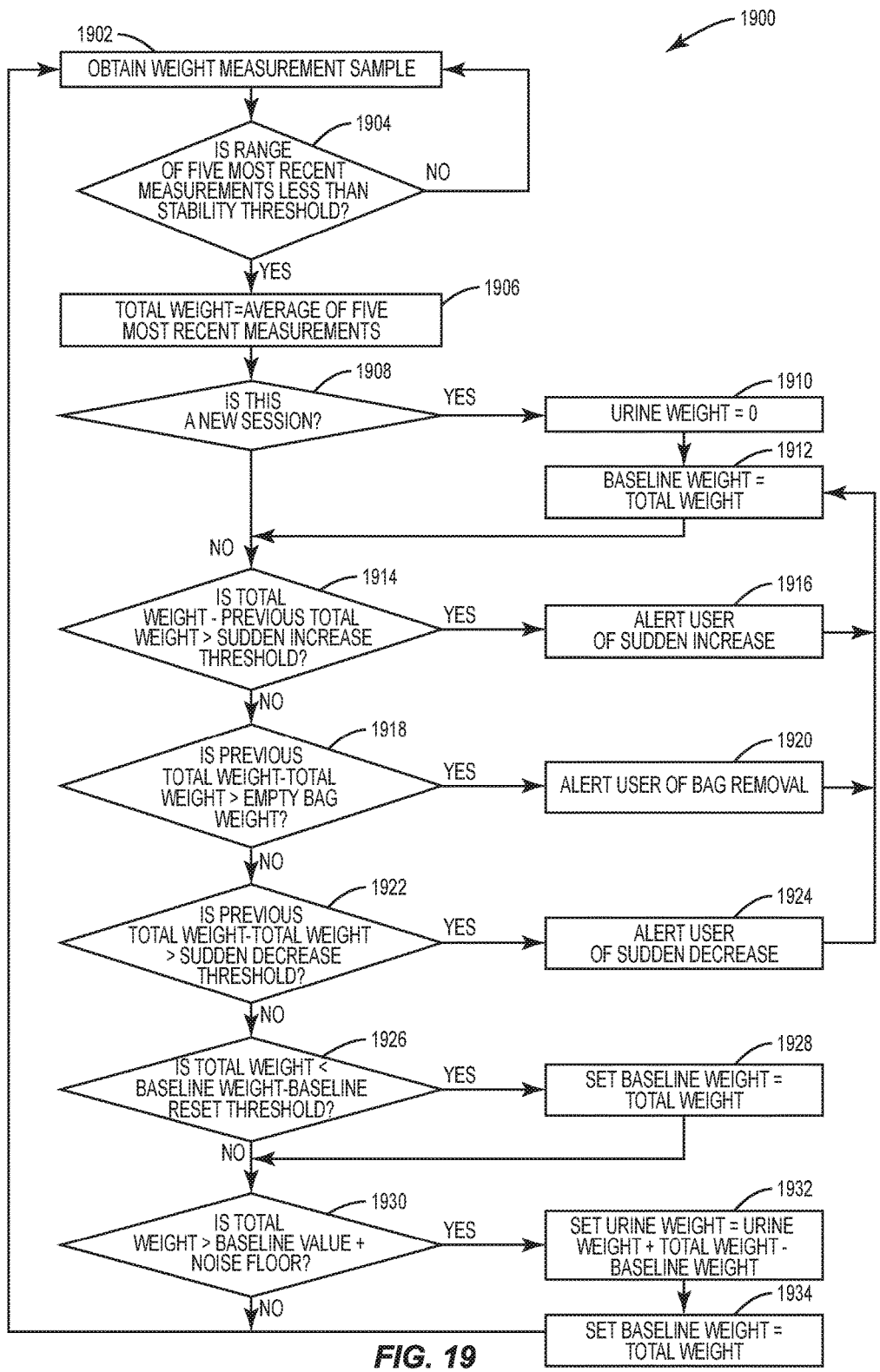
FIG. 19 is a flowchart illustrating an exemplary process carried out by the fluid container measurement systems of FIGS. 1A-18B to increase measurement accuracy by mitigating any effect of a dynamic force vector transmitted by the tube to on load cell.

FIG. 19 is a flowchart 1900 illustrating an exemplary process carried out by the fluid container measurement systems 100, 100', 100" (e.g., the measurement control circuit 208) to increase measurement accuracy by mitigating any effect of a dynamic force vector transmitted by the tube 136 on the load cell 114. A design feature of the tube 136 (also referred to as a drain tube) is their ability to resist bending, kinking, stretching, etc., while also being flexible enough to be easily routed from a patient to a urine bag. The tube 136 may be made of a flexible plastic, semi-flexible plastic, or elastomer with a tube memory (also referred to as springiness) to reduce accidental interruptions of draining caused by compression or kinking of the tube 136. Thus, when the tube 136 is deformed, the tube 136 acts like a spring and returns to a pre-bent shape. Further, the tube 136, under the influence of gravity, creeps over time to ensure that if there are accidental disruption points, then gravity would act on those disruption points and correct them. Accordingly, both tube memory and the effect of gravity may dynamically and constantly change the tube shape over time. This dynamic force vector may be transmitted by the tube 136 to the bag and the load cell 114, thereby affecting weight measurement accuracy of the fluid container measurement system 100, 100', 100". In particular, for example, after the bag is first hung from the load cell 114, the force vector transmitted by the tube 136 becomes more horizontal, which the load cell 114 may record as a reduction in weight or volume within the bag, artificially lowering the volume readings. Thus, real volume increases within the bag may be completely or partially masked by dynamic forces exerted by the tube 136 on the load cell 114. The flowchart 1900 illustrates an exemplary process to, among other things, account for these dynamic forces transmitted by the tube 136.

In step 1902 the measurement control circuit 208 obtains a weight measurement (also referred to as a load measurement, weight measurement sample, etc.). In step 1904, the measurement control circuit 208 determines whether the range of the five most recent load measurements are less than a stability threshold (also referred to as a stability threshold load measurement). However, it is noted that the range may include more or fewer measurements (e.g., two most recent measurements, ten most recent measurements, etc.). The stability threshold is a predetermined range to determine whether the measurements are fluctuating too much, such as when the fluid container 102 is being attached to or removed from the fluid container measurement system 100. If in step 1904 the measurement control circuit 208 determines the range is not less than a stability threshold, then the process reverts to step 1902. If instead the measurement control circuit 208 determines the range is less than a stability threshold, then the process proceeds to step 1906. In step 1906, the measurement control circuit 208 defines the total weight (also referred to as the total load measurement, total weight measurement, etc.) as equal to the average of the five most recent weight measurements.

In step 1908, the measurement control circuit 208 determines whether it is a new session. If it is a new session, then in step 1910, the measurement control circuit 208 defines the urine weight (also referred to as a running total, running urine weight measurement, etc.) as equal to zero, and in step 1912, the measurement control circuit defines the baseline weight (also referred to as a baseline load measurement, baseline weight measurement, etc.) as equal to the total weight. Then the process proceeds to step 1914. If in step 1908, the measurement control circuit 208 determines that the session is not new, then the process proceeds to step 1914.

In step 1914, the measurement control circuit 208 determines whether the difference between the total weight and the previous total weight is greater than a sudden increase threshold (also referred to as a sudden increase threshold measurement, etc.). If it is greater than the sudden increase threshold, then in step 1916, the measurement control circuit 208 alerts a user of the sudden increase and reverts to step 1912. If it is not greater than the sudden increase threshold, then the process proceeds to step 1918. For example, assume the time window average count is 5 ms, the baseline reset threshold is 0.25 g, the measurement stability threshold is 3 g, the noise floor is 0.25 g, the sudden increase threshold is 75 g, and the sudden decrease threshold is 10 g. A sample data set according to the above is shown in Table 1 below:

TABLE 1

| Measurement | Raw Measurement Data | Total Weight | Baseline Weight | Urine Weight | Stable? |
|---|---|---|---|---|---|
| 1 | 100 | | | | |
| 2 | 100 | | | | |
| 3 | 100 | | | | |
| 4 | 100 | | | | |
| 5 | 100 | 100 | 0 | 0 | Y |
| 6 | 180 | 116 | 0 | 0 | N |
| 7 | 180 | 132 | 0 | 0 | N |
| 8 | 180 | 148 | 0 | 0 | N |
| 9 | 180 | 164 | 0 | 0 | N |
| 10 | 180 | 180 | 180 | 0 | Y |

TABLE 1-continued

| Measurement | Raw Measurement Data | Total Weight | Baseline Weight | Urine Weight | Stable? |
|---|---|---|---|---|---|
| 11 | 180 | 180 | 180 | 0 | Y |
| 12 | 180 | 180 | 180 | 0 | Y |

According to the above, at measurement 10, the measurement control circuit 208 would alert a user to a sudden increase (after the measurement data is stable), and ask the user whether the sudden increase should be added to the urine weight.

In step 1918, the measurement control circuit 208 determines whether the difference between the previous total weight and the total weight is greater than an empty bag weight (also referred to as an empty bag weight measurement, empty bag weight load measurement, etc.). If it is greater than the empty bag weight, then in step 1920, the measurement control circuit 208 alerts a user of bag removal and the process reverts to step 1912. Accordingly, if the measurement control circuit 208 records a drop in weight greater than the bag weight, then the measurement control circuit 208 determines that the bag has been removed. If it is not greater than the empty bag weight, then the process proceeds to step 1922.

In step 1922, the measurement control circuit 208 determines whether the difference between the previous total weight and the total weight is greater than a sudden decrease threshold (also referred to as a sudden decrease threshold load measurement, etc.). If it is greater than the sudden decrease threshold, then in step 1924, the measurement control circuit 208 alerts a user of a sudden decrease, and the process reverts to step 1912. Accordingly, if the measurement control circuit 208 records a drop in weight greater than the sudden decrease threshold (but less than the empty bag weight), then the measurement control circuit 208 alerts the user to a sudden decrease. If it is not greater than the sudden decrease threshold, then the process proceeds to step 1926. For example, assume the time window average count is 5 ms, the baseline reset threshold is 0.25 g, the measurement stability threshold is 3 g, the noise floor is 0.25 g, the sudden increase threshold is 75 g, and the sudden decrease threshold is 10 g. A sample data set according to the above is shown in Table 2 below:

TABLE 2

| Measurement | Raw Measurement Data | Total Weight | Baseline Weight | Urine Weight | Stable? |
|---|---|---|---|---|---|
| 1 | 100 | | | | |
| 2 | 100 | | | | |
| 3 | 100 | | | | |
| 4 | 100 | | | | |
| 5 | 100 | 100 | 100 | 0 | Y |
| 6 | 80 | 96 | 100 | 0 | N |
| 7 | 80 | 92 | 100 | 0 | N |
| 8 | 80 | 88 | 100 | 0 | N |
| 9 | 80 | 84 | 100 | 0 | N |
| 10 | 80 | 80 | 80 | 0 | Y |
| 11 | 80 | 80 | 80 | 0 | Y |
| 12 | 80 | 80 | 80 | 0 | Y |

According to the above, at measurement 10, the measurement control circuit 208 would alert a user to a sudden decrease (after the measurement data is stable), and ask the user to reset the bag.

In step 1926, the measurement control circuit 208 determines whether the total weight is less than the difference between the baseline weight and a baseline reset threshold (also referred to as a baseline reset threshold load measurement). If it is less than the difference between the baseline weight and the baseline reset threshold, then in step 1928, the measurement control circuit 208 defines the set baseline weight as the total weight, and the process proceeds to step 1930. Accordingly, the measurement control circuit 208 determines that small decreases in total weight are due to the tube 136 impart a force upon the load cell 114 as the tube 136 settles or relaxes, which may take second, minutes, or hours. If it is not less than the difference between the baseline weight and the baseline reset threshold, then the process proceeds to step 1930. For example, assume the time window average count is 5 ms, the baseline reset threshold is 0.25 g, the measurement stability threshold is 3 g, the noise floor is 0.25 g, the sudden increase threshold is 75 g, and the sudden decrease threshold is 10 g. A sample data set according to the above is shown in Table 3 below:

TABLE 3

| Measurement | Raw Measurement Data | Total Weight | Baseline Weight | Urine Weight | Stable? |
|---|---|---|---|---|---|
| 1 | 100 | | | | |
| 2 | 100 | | | | |
| 3 | 100 | | | | |
| 4 | 100 | | | | |
| 5 | 100 | 100 | 100 | 0 | Y |
| 6 | 99 | 99.8 | 100 | 0 | Y |
| 7 | 99 | 99.6 | 99.6 | 0 | Y |
| 8 | 99 | 99.4 | 99.6 | 0 | Y |
| 9 | 99 | 99.2 | 99.2 | 0 | Y |
| 10 | 99 | 99 | 99.2 | 0 | Y |

According to the above, between measurement 1 and measurement 10, the measurement control circuit 208 observes a decrease in urine weight, but assumes the decrease is the result of a change in force imparted by the tube 136.

In step 1930, the measurement control circuit 208 determines whether the total weight is greater than the combination of the baseline value and a noise floor. If it is greater, then in step 1932, the measurement control circuit 208 defines the urine weight as equal to the urine weight plus the total weight minus the baseline weight (where the total weight minus the baseline weight is the additional urine weight detected, thus keeping a running total of urine weight). In step 1934, the measurement control circuit 208 defines the baseline weight as the total weight, and the process reverts to step 1902. Accordingly, the measurement control circuit 208 determines that increases in total weight above a noise floor are the result of urine entering the fluid container 102. Otherwise, if the measurement control circuit 208 determines it is not greater, then the process reverts to step 1902. For example, assume the time window average count is 5 ms, the baseline reset threshold is 0.25 g, the measurement stability threshold is 3 g, the noise floor is 0.25 g, the sudden increase threshold is 75 g, and the sudden decrease threshold is 10 g. A sample data set according to the above is shown in Table 4 below:

TABLE 4

| Measurement | Raw Measurement Data | Total Weight | Baseline Weight | Urine Weight | Stable? |
|---|---|---|---|---|---|
| 1 | 100 | | | | |
| 2 | 100 | | | | |
| 3 | 100 | | | | |
| 4 | 100 | | | | |
| 5 | 100 | 100 | 100 | 0 | Y |
| 6 | 102 | 100.4 | 100.4 | 0.4 | Y |
| 7 | 104 | 101.2 | 100.4 | 0.4 | N |
| 8 | 106 | 102.4 | 100.4 | 0.4 | N |
| 9 | 106 | 103.6 | 100.4 | 0.4 | N |
| 10 | 106 | 104.8 | 100.4 | 0.4 | N |
| 11 | 106 | 105.6 | 105.6 | 5.6 | Y |
| 12 | 106 | 106 | 106 | 6 | Y |

According to the above, between measurement 1 and measurement 12, the measurement control circuit 208 records the addition of urine weight to the running total.

Figure 20:
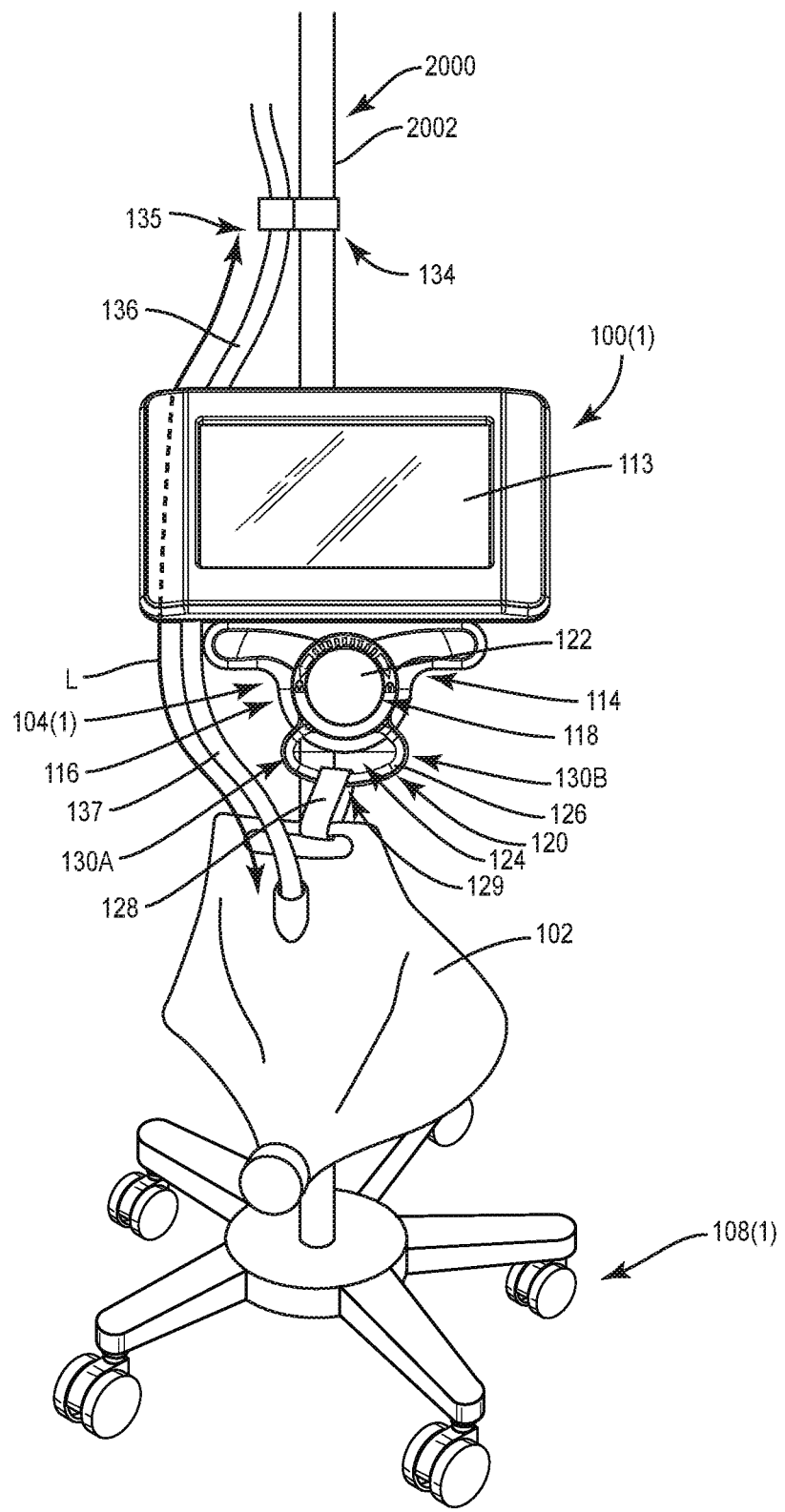
FIG. 20 is a side perspective view of the fluid container measurement system in FIGS. 1A and 1B with an alternative tether support system that includes a tether support member secured to the tube of the fluid container and secured to a device other than the fluid container measurement system.

Other options are possible to support the tube 136 of the fluid container 102 measured by a fluid container measurement system other than on the load measurement assembly 104. For example, FIG. 20 is a side perspective view of an alternative fluid container measurement system 100(1) that includes a load measurement assembly 104(1). Common elements between the fluid container measurement system 100(1) in FIG. 20 and the fluid container measurement system 100 in FIGS. 1A and 1B are shown with common element numbers and thus will not be re-described. As shown in FIG. 17, an external device 2000, such as an IV pole 2002, is shown, which may be commonly available in medical settings in particular where the fluid container 102 is located to dispense fluid to or collect drained fluid from a patient. The tether support member 134 shown in FIGS. 15A-15D, or other attachment means, may be provided and configured to be attached or mounted to external device 2000 in FIG. 20. Again, as discussed previously with regard to FIGS. 13A and 13B, the tether support member 134 is configured to support the tube 136 of the fluid container 102 in the support area 135 of the tube 136 to the external device 2000 in this example. This allows a predefined length L of the tube 136 to be supported by the support member 120 as part of the weight of the fluid container 102. Further, the predefined length L of the supported portion 137 of the tube 136 can be selected to provide slack in the supported portion 137 of the tube 136 when supported by the tether support member 134, so that a strain is avoided in the supported portion 137 of the tube 136. Thus, a force from the external device 2000 is not imparted on the fluid container 102 due from strain.

Figure 21:
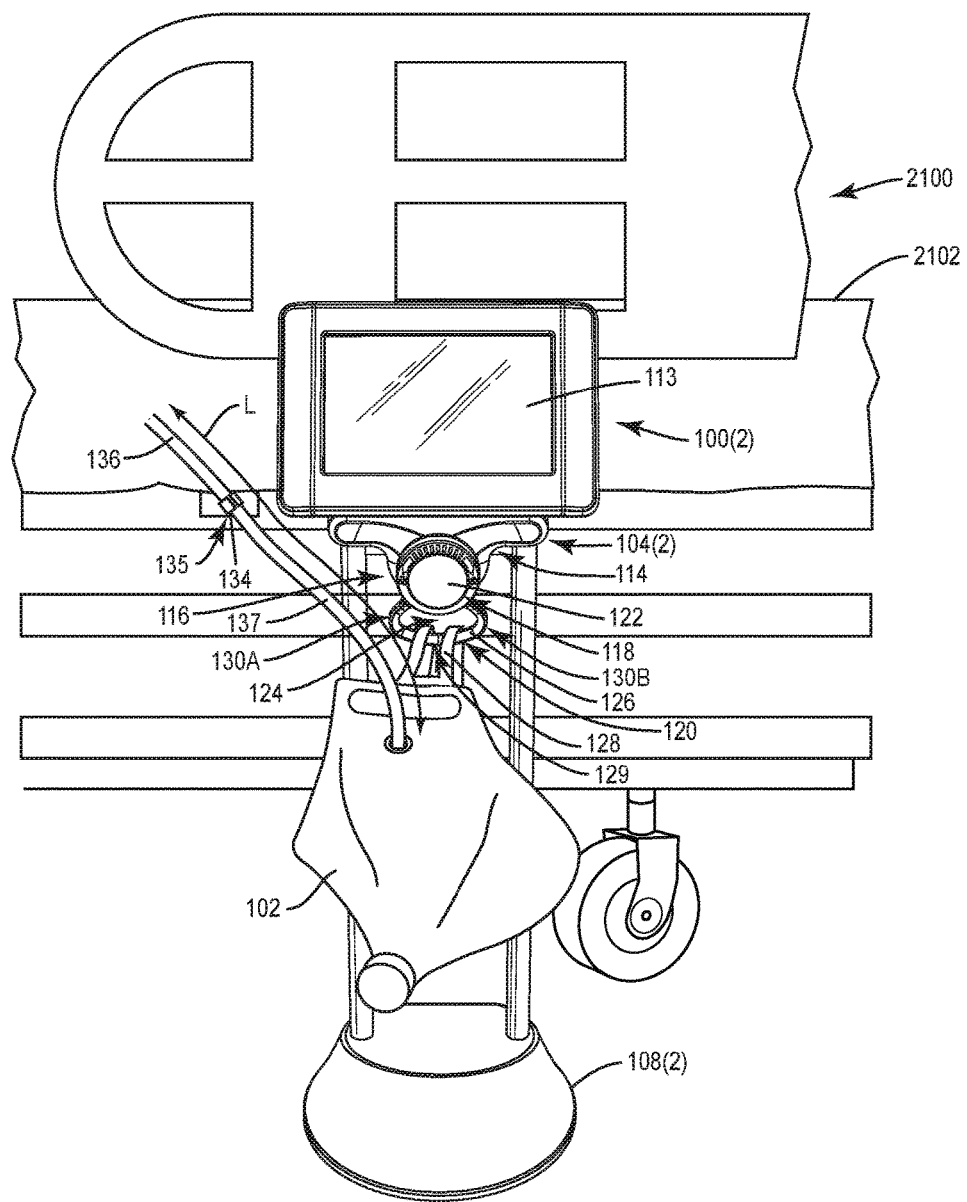
FIG. 21 is a side perspective view of the fluid container measurement system in FIGS. 1A and 1B with another alternative tether support system that includes a tether support member secured to the tube of the fluid container and secured to a device other than the fluid container measurement system.

FIG. 21 is a side perspective view of another alternative fluid container measurement system 100(2) that includes a load measurement assembly 104(2). Common elements between the fluid container measurement system 100(2) in FIG. 21 and the fluid container measurement system 100 in FIGS. 1A and 1B are shown with common element numbers and thus will not be re-described. As shown in FIG. 21, an external device 2100, such as a bed 2102 is shown, which may be commonly available in medical settings in particular where the fluid container 102 is located to dispense fluid to or collect drained fluid from a patient. The tether support member 134 shown in FIGS. 14A and 14B, or other attachment means, may be provided and configured to be attached or mounted to the bed 2102. Again, as discussed previously with regard to FIGS. 13A and 13B, the tether support member 134 is configured to support the tube 136 of the fluid container 102 in the support area 135 of the tube 136 to the external device 2100 in this example. This allows a predefined length L of the supported portion 137 of the tube 136 to be supported by the support member 120 as part of the weight of the fluid container 102. Further, the predefined length L can be selected to provide slack in the supported portion 137 of the tube 136 when supported by the tether support member 134, so that a strain is avoided in the supported portion 137 of the tube 136. Thus, a force from the external device 2100 is not imparted on the fluid container 102 from strain.

Figure 22:
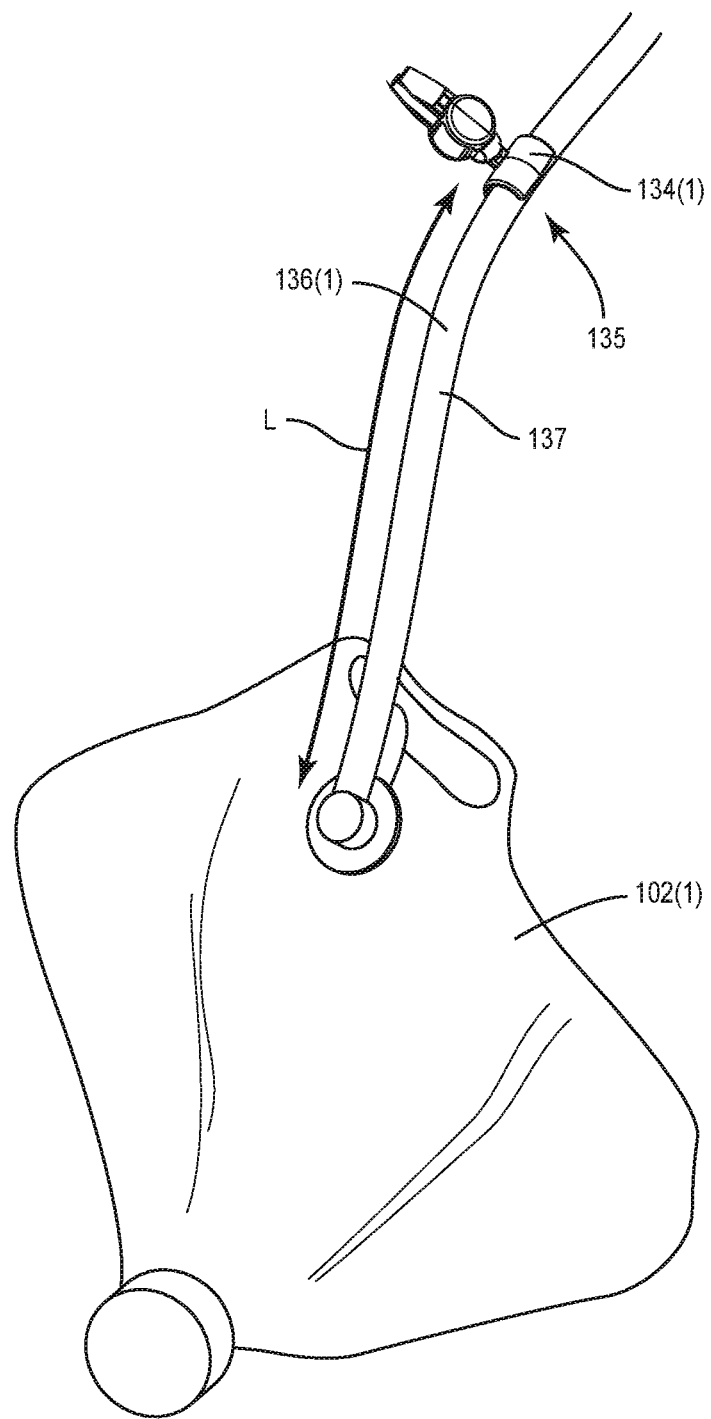
FIG. 22 is a fluid container with an integrated tube that includes an integrated tether support member for supporting the tube.

The examples of the tether support member 134 above provide the tether support member 134 as a separate component from the tube 136. As discussed above, the tube 136 is inserted into the slot member 138 of the tether support member 134 to support the tube 136. As an alternative arrangement, the tether support member 134 could be integrated into or already secured to the tube 136 of the fluid container 102. For example, the tether support member 134 could be integrated into or secured to the tube 136 of the fluid container 102 as part of the manufacturing of the fluid container 102. In this manner, the support area 135 of the tube 136 is predefined without the user having to determine the support area 135. Different fluid containers 102 have different designs and dimensions such that the desired support area 135 to provide the desired supported portion 137 of the tube 136 is different for different types of fluid containers 102. In this regard, FIG. 22 is a fluid container 102(1) with a tube 136(1) that includes an integrated tether support member 134(1) at a support area 135 to facilitate support of the tube 136 when installed on a fluid container measurement system, including those described above. The tether support member 134(1) can be overmolded, secured by glue or epoxy, or integrated as part of the tube 136, as examples of integration of the tether support member 134(1) to the tube 136.

Those of skill in the art will further appreciate that the various illustrative logical blocks, modules, circuits, and algorithms described in connection with the aspects disclosed herein may be implemented as electronic hardware, instructions stored in memory or in another computer-readable medium and executed by a processor or other processing device, or combinations of both. The master and slave devices described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends upon the particular application, design choices, and/or design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the aspects disclosed herein may be implemented or performed with a processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The aspects disclosed herein may be embodied in hardware and in instructions that are stored in hardware, and may reside, for example, in Random Access Memory (RAM), flash memory, Read Only Memory (ROM), Electrically Programmable ROM (EPROM), Electrically Erasable Programmable ROM (EEPROM), registers, a hard disk, a removable disk, a CD-ROM, or any other form of computer readable medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

It is also noted that the operational steps described in any of the exemplary aspects herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary aspects may be combined. It is to be understood that the operational steps illustrated in the flow chart diagrams may be subject to numerous different modifications as will be readily apparent to one of skill in the art. Those of skill in the art will also understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

What is claimed is:

1. A fluid container measurement system, comprising:
   a load measurement assembly comprising:
      a load cell having a principal load axis substantially orthogonal to a ground; and
      a measurement control circuit electrically coupled to the load cell, the measurement control circuit configured to receive electrical signals from the load cell indicative of a force imposed on the load cell;
   a support member mechanically linked to the load cell, the support member configured to support a fluid container such that a downward force applied by a weight of the fluid container on the support member is applied to the load cell to determine the weight of the fluid container; and at least one strain relief configured to support a length of a tube in fluid communication with the fluid container to reduce a strain force of a supported portion of the tube and prevent the strain force from unduly influencing the force imposed on the load cell.

2. The fluid container measurement system of claim 1, wherein the support member comprises a concave-shaped member configured to support the fluid container.

3. The fluid container measurement system of claim 1, further comprising a display attached to the load measurement assembly, the display electrically coupled to the measurement control circuit.

4. The fluid container measurement system of claim 1, further comprising a housing; wherein the load measurement assembly is mounted to the housing.

5. The fluid container measurement system of claim 4, wherein the at least one strain relief is attached to the housing.

6. The fluid container measurement system of claim 4, wherein the at least one strain relief is integrally attached to the housing.

7. The fluid container measurement system of claim 4, wherein the at least one strain relief is unattached and separate from the housing.

8. The fluid container measurement system of claim 1, wherein the at least one strain relief comprises a semicircular inside surface.

9. The fluid container measurement system of claim 1, wherein the at least one strain relief comprises a slot member configured to receive the tube.

10. The fluid container measurement system of claim 1, wherein the at least one strain relief comprises a first set of strain reliefs and a second set of strain reliefs.

11. The fluid container measurement system of claim 10, further comprising a first sensor positioned between two first strain reliefs of the first set of strain reliefs and a second sensor positioned between two second strain reliefs of the second set of strain reliefs, the first and second sensors configured to detect whether the tube is secured to at least one strain relief of at least one of the first set of strain reliefs and the second set of strain reliefs.

12. The fluid container measurement system of claim 1, further comprising a sensor configured to detect whether the tube is secured to the at least one strain relief.

13. The fluid container measurement system of claim 12, wherein the sensor is positioned within the at least one strain relief.

14. The fluid container measurement system of claim 12, wherein the sensor comprises an optical sensor.

15. The fluid container measurement system of claim 12, wherein the sensor comprises an infrared sensor.

16. The fluid container measurement system of claim 1, further comprising a fluid container assembly connected to the support member, the fluid container assembly comprising:
the fluid container;
the tube connected to and extending from the fluid container, the tube in fluid communication with the fluid container; and
an indicator positioned on the tube at a predetermined length from the fluid container for detection by a sensor of a fluid container measurement system.

17. The fluid container measurement system of claim 16, wherein the indicator is at least one of a bar code, an RFID tag, a predefined ink composition, or a predefined color.

18. The fluid container measurement system of claim 16, wherein the indicator comprises an optic ribbon.

19. The fluid container measurement system of claim 18, wherein the optic ribbon is opaque.

20. The fluid container measurement system of claim 18, wherein the optic ribbon is a predefined color.

21. The fluid container measurement system of claim 18, wherein the optic ribbon is white.

22. The fluid container measurement system of claim 18, wherein the optic ribbon comprises a head.

23. The fluid container measurement system of claim 22, further comprising an optic ribbon assembly comprising the optic ribbon and a first tape strip at the head to affix the head on the tube.

24. The fluid container measurement system of claim 22, wherein the optic ribbon comprises a body, the head at a first end of the body.

25. The fluid container measurement system of claim 24, wherein a body length of the body corresponds to the predetermined length for positioning the head on the tube.

26. The fluid container measurement system of claim 25, further comprising an optic ribbon assembly comprising the optic ribbon and a first tape strip at a second end of the body.

27. The fluid container measurement system of claim 26, wherein the optic ribbon assembly further comprises a second tape strip at the first end of the body.

28. The fluid container measurement system of claim 1, wherein the measurement control circuit is configured to:
obtain a load measurement from the load cell; wherein
if the load measurement is less than a difference between a previous baseline load measurement and a baseline reset threshold load measurement, set a new baseline load measurement equal to the load measurement; and
if the load measurement is greater than the previous baseline load measurement plus a noise floor threshold load measurement:
add a difference between the load measurement and the previous baseline load measurement to a running total; and
set a new baseline load measurement equal to the load measurement.

29. The fluid container measurement system of claim 28, wherein the load measurement comprises an average of a plurality of recent load measurements.

30. The fluid container measurement system of claim 29, wherein the load measurement control circuit is further configured to obtain additional recent load measurements if a range of the plurality of recent load measurements is not less than a stability threshold.

31. The fluid container measurement system of claim 28, wherein the measurement control circuit is further configured to alert a user of a sudden increase if a difference between the load measurement and a previous load measurement is greater than a sudden increase threshold.

32. The fluid container measurement system of claim 28, wherein the measurement control circuit is further configured to alert a user of a fluid container removal if a difference between a previous load measurement and the load measurement is greater than an empty fluid container weight.

33. The fluid container measurement system of claim 28, wherein the measurement control circuit is further configured to alert a user of a sudden decrease if a difference between a previous load measurement and the load measurement is greater than a sudden decrease threshold load measurement.

34. The fluid container measurement system of claim 28, wherein:
the load measurement comprises a weight measurement; and
the previous baseline load measurement comprises a baseline weight measurement.

35. The fluid container measurement system of claim 28, wherein the running total comprises a running total of urine weight.

36. A fluid container assembly, comprising:
a fluid container configured for mounting to a support member of a fluid container measurement system comprising a sensor;
a tube connected to and extending from the fluid container, the tube is in fluid communication with the fluid container; and
an indicator comprising an optic ribbon positioned on the tube at a length from the fluid container for detection by the sensor of the fluid container measurement system, the length corresponding to a supported portion of the tube to be supported by the support member of the fluid container measurement system to reduce a strain force of the supported portion of the tube and prevent the strain force from unduly influencing a force imposed on a load cell.

37. The fluid container assembly of claim 36, wherein the indicator is at least one of a bar code, an RFID tag, a predefined ink composition, or a predefined color.

38. The fluid container assembly of claim 36, wherein the optic ribbon is opaque.

39. The fluid container assembly of claim 36, wherein the optic ribbon is a predefined color.

40. The fluid container assembly of claim 36, wherein the optic ribbon is white.

41. The fluid container assembly of claim 36, wherein the optic ribbon comprises a head.

42. The fluid container assembly of claim 41, further comprising an optic ribbon assembly comprising the optic ribbon and a first tape strip at the head to affix the head on the tube.

43. The fluid container assembly of claim 42, wherein the optic ribbon comprises a body, the head at a first end of the body.

44. The fluid container assembly of claim 43, wherein a body length of the body corresponds to the length for positioning the head on the tube.

45. The fluid container assembly of claim 44, wherein the optic ribbon assembly further comprises a second tape strip at the first end of the body.

46. A method of measuring a fluid container, comprising:
attaching a fluid container to be measured to a support member of a fluid container measurement system;
attaching a tube in fluid communication with the fluid container to at least one strain relief to support a predefined length of the tube to reduce a strain force of a supported portion of the tube;
obtaining a load measurement, by a measurement control circuit in a load measurement assembly of the fluid container measurement system, by measuring the fluid container based on an electrical signal received from a load cell indicative of a force of the fluid container imposed on the load cell, the load cell having a principal load axis substantially orthogonal to a ground, the at least one strain relief preventing the strain force from unduly influencing the force imposed on the load cell;
setting, by the measurement control circuit, a new baseline load measurement equal to the load measurement if the load measurement is less than a difference between a previous baseline load measurement and a baseline reset threshold load measurement;
adding, by the measurement control circuit, a difference between the load measurement and the previous baseline load measurement to a running total if the load measurement is greater than the previous baseline load measurement plus a noise floor threshold load measurement; and
setting, by the measurement control circuit, a new baseline load measurement equal to the load measurement if the load measurement is greater than the previous baseline load measurement plus the noise floor threshold load measurement.

47. The method of claim 46, further comprising displaying results on a display attached to the load measurement assembly and electrically coupled to the measurement control circuit.

48. The method of claim 46, further comprising detecting, by a sensor of the load measurement assembly, whether the tube is secured to the at least one strain relief.

49. The method of claim 46, further comprising detecting, by a sensor of the load measurement assembly, whether the tube is secured to the at least one strain relief by detecting an indicator positioned on the tube at a predetermined length from the fluid container.

50. The method of claim 49, wherein the indicator is at least one of a bar code, an RFID tag, a predefined ink composition, or a predefined color.

51. The method of claim 49, wherein the indicator comprises an optic ribbon.

52. The method of claim 46, wherein the load measurement comprises an average of a plurality of recent load measurements.

53. The method of claim 52, further comprising obtaining, by the measurement control circuit, additional recent load measurements if a range of the plurality of recent load measurements is not less than a stability threshold load measurement.

54. The method of claim 46, further comprising alerting, by the measurement control circuit, a user of a sudden increase if a difference between the load measurement and a previous load measurement is greater than a sudden increase threshold load measurement.

55. The method of claim 46, further comprising alerting, by the measurement control circuit, a user of a fluid container removal if a difference between a previous load measurement and the load measurement is greater than an empty fluid container weight.

56. The method of claim 46, further comprising alerting, by the measurement control circuit, a user of a sudden decrease if a difference between a previous load measurement and the load measurement is greater than a sudden decrease threshold load measurement.

57. The method of claim 46, wherein:
the load measurement comprises a weight measurement; and
the previous baseline load measurement comprises a baseline weight measurement.

58. The method of claim 46, wherein the running total comprises a running total of urine weight.

* * * * *